US009376468B2

(12) United States Patent
Divita et al.

(10) Patent No.: US 9,376,468 B2
(45) Date of Patent: Jun. 28, 2016

(54) CELL PENETRATING PEPTIDES FOR INTRACELLULAR DELIVERY OF MOLECULES

(75) Inventors: Gilles Divita, Mauguio (FR); Karidia Konate, Montpellier (FR); May Catherine Morris, Mauguio (FR); Sebastien Deshayes, Montpellier (FR)

(73) Assignee: Aadigen, LLC, Pacific Palisades, CA (US)

( * ) Notice: Subject to any disclaimer, the term of this patent is extended or adjusted under 35 U.S.C. 154(b) by 0 days.

(21) Appl. No.: 14/009,648

(22) PCT Filed: Apr. 4, 2012

(86) PCT No.: PCT/IB2012/051665
§ 371 (c)(1),
(2), (4) Date: Feb. 20, 2014

(87) PCT Pub. No.: WO2012/137150
PCT Pub. Date: Oct. 11, 2012

(65) Prior Publication Data
US 2014/0227344 A1 Aug. 14, 2014

(30) Foreign Application Priority Data
Apr. 4, 2011 (WO) .................. PCT/IB2011/051435

(51) Int. Cl.

| | |
|---|---|
| *C07K 7/08* | (2006.01) |
| *A61K 31/713* | (2006.01) |
| *A61K 47/48* | (2006.01) |
| *C12N 15/11* | (2006.01) |

(52) U.S. Cl.
CPC ................. *C07K 7/08* (2013.01); *A61K 31/713* (2013.01); *A61K 47/48038* (2013.01); *A61K 47/48046* (2013.01); *A61K 47/48215* (2013.01); *A61K 47/48246* (2013.01); *A61K 47/48884* (2013.01); *C12N 15/111* (2013.01); *C12N 2310/14* (2013.01); *C12N 2310/3513* (2013.01); *C12N 2320/32* (2013.01)

(58) Field of Classification Search
None
See application file for complete search history.

(56) References Cited

U.S. PATENT DOCUMENTS

2009/0281041 A1* 11/2009 Debnath et al. ................. 514/13
2010/0111898 A1 5/2010 Pelura
2015/0080320 A1 3/2015 Desai

FOREIGN PATENT DOCUMENTS

WO WO-03/056013 A1 7/2003
WO 2007/069090 6/2007
WO 2008/036929 3/2008
WO WO-2011/153323 A2 12/2011
WO WO-2011/153323 A3 12/2011
WO WO-2013/173307 A1 11/2013
WO WO-2014/053624 A1 4/2014
WO WO-2014/053880 A1 4/2014

OTHER PUBLICATIONS

Crombez et al. (Targeting cyclin B1 through peptide-based delivery of siRNA prevents tumour growth; Nucleic Acids Research, 2009. vol. 37, No. 14 4559-4569).*

Crombez, L. et al. (Jan. 2009). "A New Potent Secondary Amphipathic Cell-Penetrating Peptide for siRNA Delivery Into Mammalian Cells," *Mol. Ther.* 17(1):95-103.

Deshayes, S. et al. (2005). "Cell-penetrating Peptides: Tools for Intracellular Delivery of Therapeutics," *Cell Mol Life Sci.* 62:1839-1849.

Deshayes, S. et al. (2008, e-pub. Oct. 25, 2007). "Delivery of Proteins and Nucleic Acids Using a Non-Covalent Peptide-Based Strategy," *Adv. Drug Deliv. Rev.* 60:537-547.

Glover, D.J. et al. (Apr. 2005, e-pub. Mar. 10, 2005). "Towards Safe, Non-Viral Therapeutic Gene Expression in Humans," *Nat. Rev. Genet.* 6:299-310.

Gondeau, C. et al. (Apr. 2005, e-pub. Jan. 11, 2005). "Design of a Novel Class of Peptide Inhibitors of Cyclin-Dependent Kinase/ Cyclin Activation," *J.BioL Chem.* 280(14):13793-13800.

He, L, et al. (2007) "A MicroRNA Component of the p53 Tumour Suppressor network," *Nature* 447(7148):1130-1134.

Heitz, F. et al. (2009). "Themed Section: Vector Design and Drug Delivery Review. Twenty Years of Cell-Penetrating Peptides: From Molecular Mechanisms to Therapeutics," *British Journal of Pharmacology* 157:195-206.

Ji, Q. et al. (Aug. 28, 2009). MicroRNA miR-34 Inhibits Human Pancreatic Cancer Tumor-Initiating Cells, *PLoS One* 4(8):e6816, pp. 1-13.

Kim, Y-W. et al. (2011, e-pub. May 12, 2011). "Synthesis of All-Hydrocarbon Stapled a-Helical Peptides by Ring-Closing Olefin Methathesis," *Nature Protocols* 6(6):761-771.

(Continued)

*Primary Examiner* — James H Alstrum Acevedo
*Assistant Examiner* — Tara Martinez
(74) *Attorney, Agent, or Firm* — Morrison & Foerster LLP

(57) ABSTRACT

The présent invention relates to cell-penetrating peptides char-acterized in that it comprises an amino acid séquence selected in the group consisting of X1LX2RALWX9LX3X9X4LWX9LX5X6X7X8, X1LX2LARWX9LX3X9X4LWX9LX5X6X7X8 and X1LX2ARLWX9LX3X9X4LWX9LX5X6X7X8, wherein X1 is beta-A or S, X2 is F or W, X3 is L, W, C or I, X4 is S, A, N or T, Xs is L or W, X6 is W or R, X7 is K or R, X8 is A or none, and X9 is R or S. Thèse peptides exhibit high efficiency, low toxicity and a natural tropism for lung tissues, and can be used either in simple complex with the cargo to be vectorised, or in nanoparticles comprising two layers of cell-penetrating peptides around the cargo.

34 Claims, 17 Drawing Sheets

(56) References Cited

OTHER PUBLICATIONS

Figure 1:
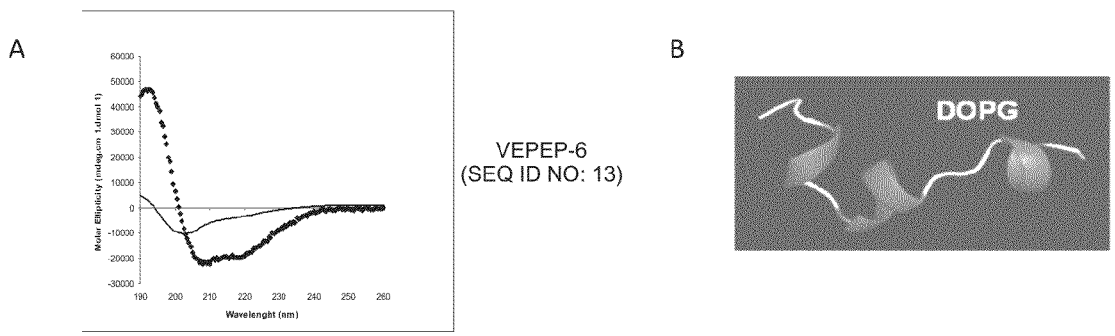

Kurzawa, L. et al. (2010). "PEP and CADY-mediated 1-23 delivery of fluorescent peptides and proteins into living cells," *Biochimica Et Biophysica Acta* 1798(12):2274-2285.

Mery, J. et al. (Jul./Aug. 1992). "Disulfide Bond as Peptide-Resin Linkage in Boc-Bzl SPPS, for Potential Biochemical Applications," *Pept Res.* 5(4):233-40.

Morris, M.C. et al. (1997). "A New Peptide Vector for Efficient Delivery of Oligonucleotides Into Mammalian Cells," *Nucleic Acids Res.* 25(14):2730-2736.

Morris, M.C. et al. (Dec. 2001). "A Peptide Carrier for the Delivery of Biologically Active Proteins Into Mammalian Cells," *Nat. Biotechnol.* 19:1173-1176.

Takabatake et al. (2005, e-pub. Feb. 24, 2005). "Exploring RNA Interferences as a Therapeutic Strategy for Renal Disease," *Gene Therapy* 12:965-973.

Thomas, A. et al. (2006, e-pub. Oct. 3, 2006). "Prediction of Peptide Structure: How Far are We,?" *Proteins* 65:889-897.

Verdine, G.L. et al. (2012). "Stapled Peptides for Intracellular Drug Targets," Chapter 1 in *Methods in Enzymology*, 503:3-33.

Whitehead, K.A. et al. (Feb. 2009). "Knocking Down Barriers: Advances in siRNA Delivery," *Nat Rev. Drug Discov.* 8:129-138.

Zhang, H. et al. (2011). "Antiviral Activity of α-Helical Stapled Peptides Designed from the HIV-1 Capsid Dimerization Domain," *Retrovirology* 8:28, pp. 1-18.

International Search Report mailed on Nov. 7, 2012, for PCT Application No. PCT/IB2012/051665, filed on Apr. 4, 2012, 7 pages.

Written Opinion mailed on Nov. 7, 2012, for PCT Application No. PCT/IB2012/051665, filed on Apr. 4, 2012, 9 pages.

U.S. Appl. No. 14/433,573, internationally filed Oct. 4, 2013, by Divita et al. (Copy not attached).

U.S. Appl. No. 14/433,570, internationally filed Oct. 4, 2013, by Divita et al. (Copy not attached).

U.S. Appl. No. 14/433,578, internationally filed Oct. 4, 2013, by Divita et al. (Copy not attached).

U.S. Appl. No. 14/433,592, internationally filed Oct. 4, 2013, by Divita et al. (Copy not attached).

\* cited by examiner

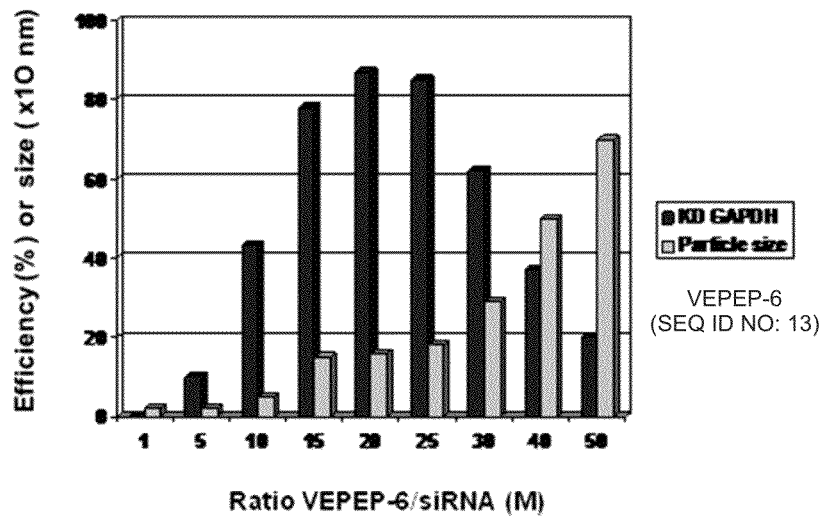
Figure 4
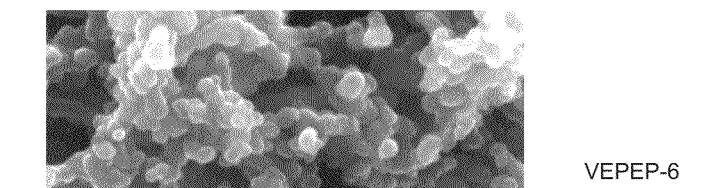
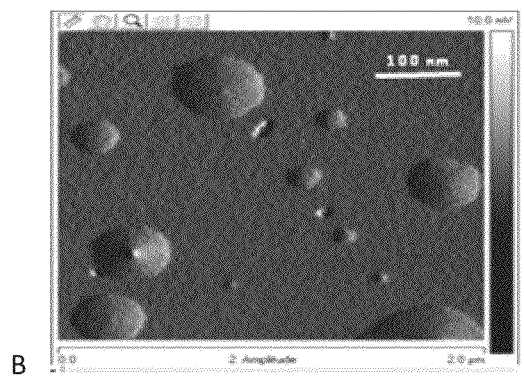
Figure 5

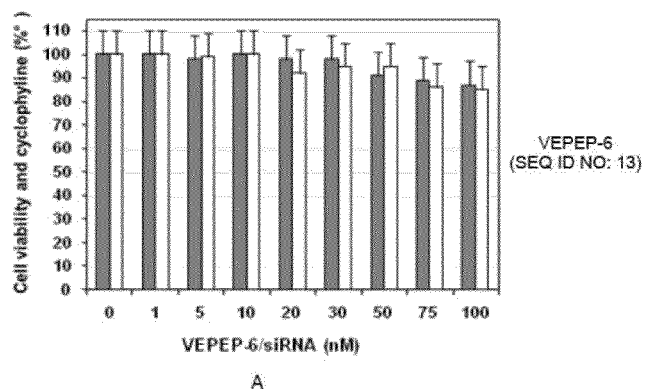
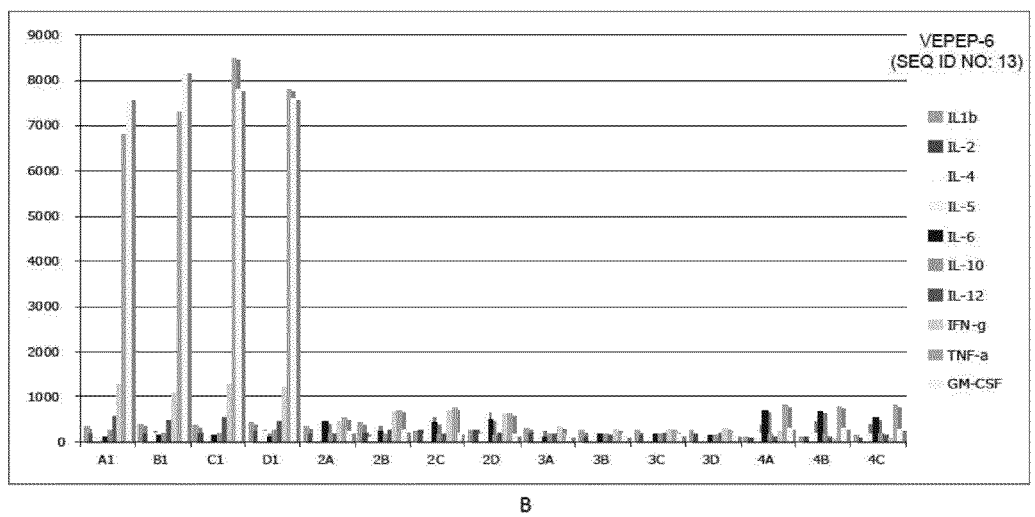
Figure 7

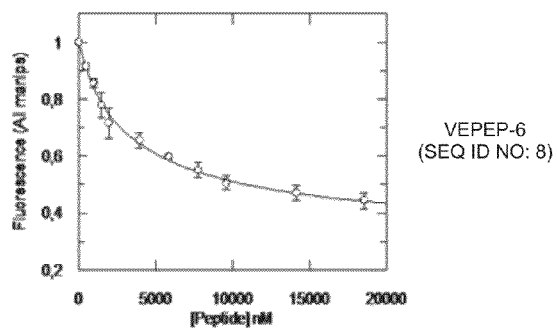
A
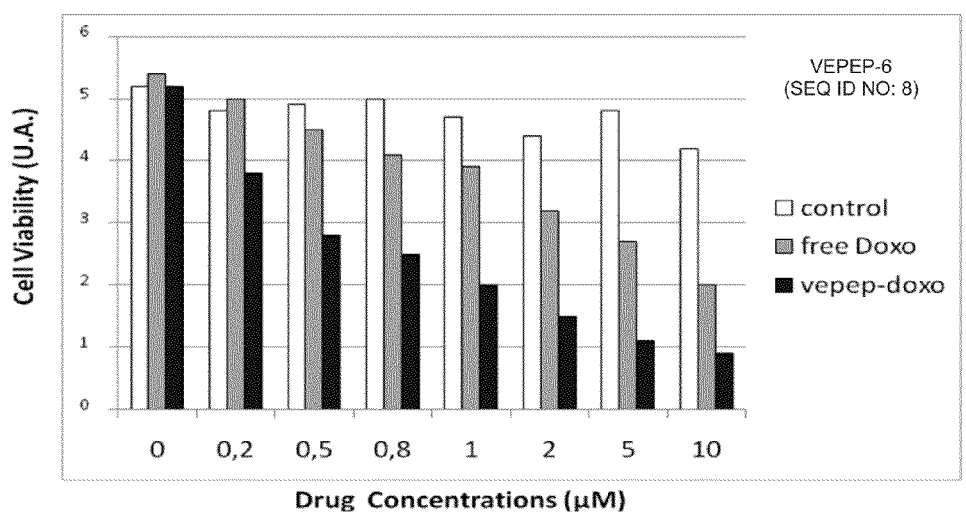
B
Figure 8

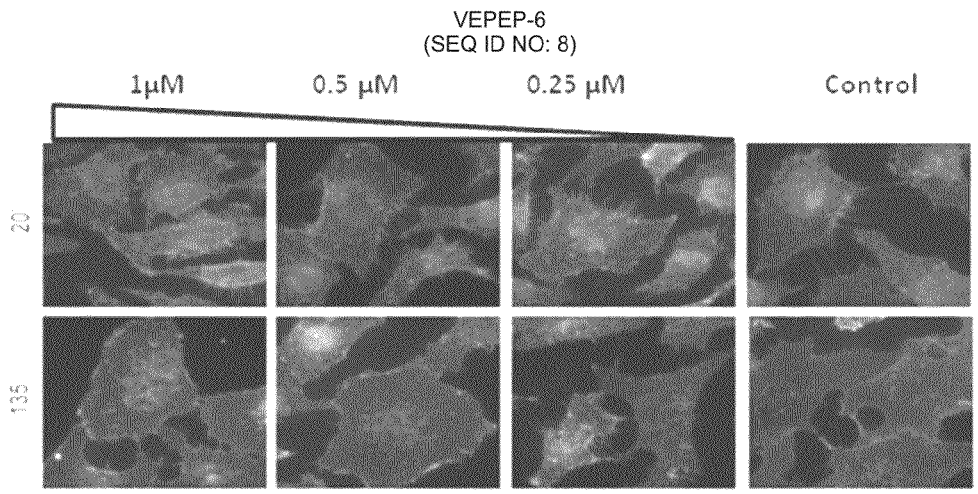
Figure 9
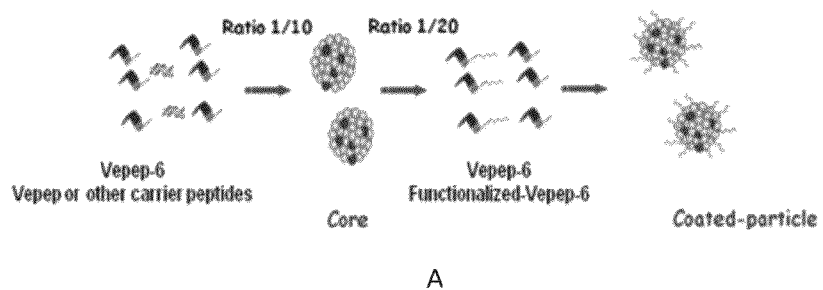
A
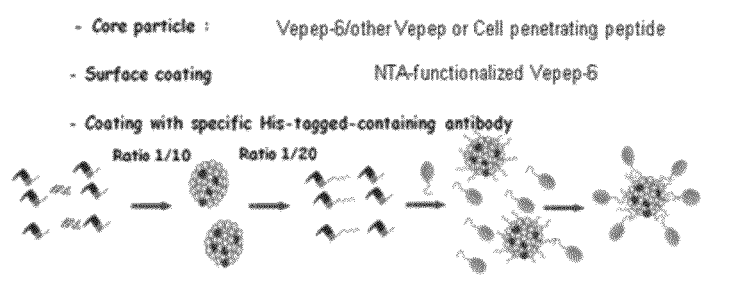
B
Figure 10

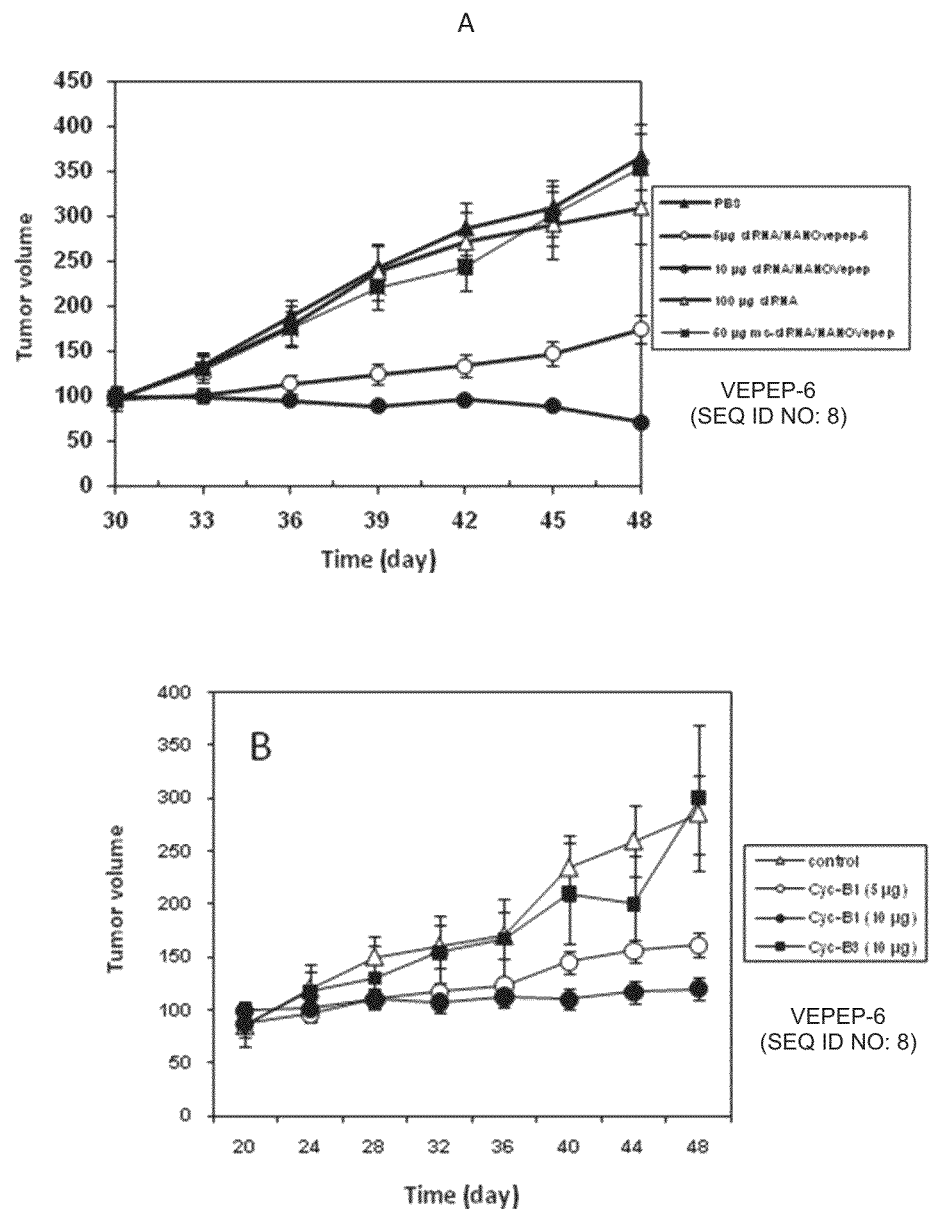
Figure 11 (A&B)

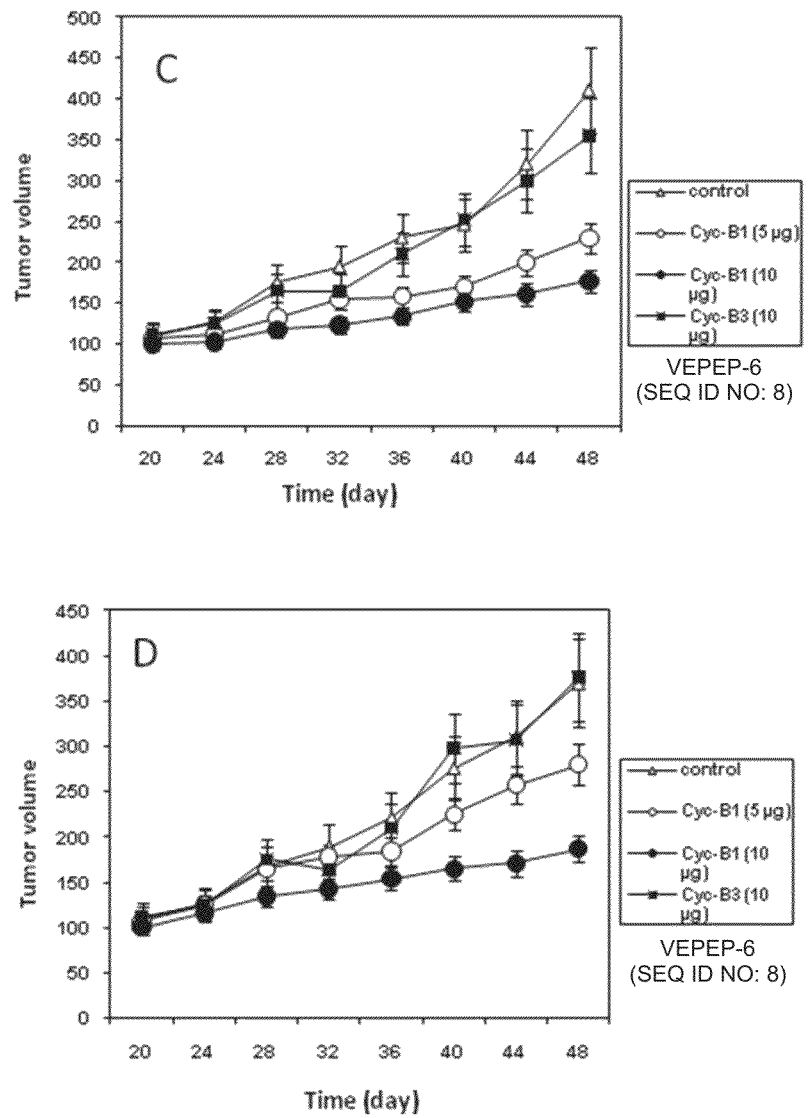
Figure 11 (C&D)

SEQUENCE LISTING

```
<160> NUMBER OF SEQ ID NOS: 38

<210> SEQ ID NO 1
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Residue is acylated on the N-terminal end
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (19)..(19)
<223> OTHER INFORMATION: Cysteamide is attached on the C-terminal end of
      the residue

<400> SEQUENCE: 1

Xaa Leu Phe Arg Ala Leu Trp Arg Leu Leu Arg Ser Leu Trp Arg Leu
1               5                   10                  15

Leu Trp Lys

<210> SEQ ID NO 2
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Residue is acylated on the N-terminal end
<220> FEATURE:
```

-continued

```
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: Cysteamide is attached on the C-terminal end of
      the residue

<400> SEQUENCE: 2

Xaa Leu Trp Arg Ala Leu Trp Arg Leu Trp Arg Ser Leu Trp Arg Leu
1               5                   10                  15

Leu Trp Lys Ala
            20

<210> SEQ ID NO 3
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Residue is acylated on the N-terminal end
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: Cysteamide is attached on the C-terminal end of
      the residue

<400> SEQUENCE: 3

Xaa Leu Trp Arg Ala Leu Trp Arg Leu Leu Arg Ser Leu Trp Arg Leu
1               5                   10                  15

Trp Arg Lys Ala
            20

<210> SEQ ID NO 4
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Residue is acylated on the N-terminal end
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: Cysteamide is attached on the C-terminal end of
      the residue

<400> SEQUENCE: 4

Xaa Leu Trp Arg Ala Leu Trp Arg Leu Trp Arg Ser Leu Trp Arg Leu
1               5                   10                  15

Trp Arg Lys Ala
            20

<210> SEQ ID NO 5
<211> LENGTH: 20
<212> TYPE: PRT
```

```
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Residue is acylated on the N-terminal end
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: Cysteamide is attached on the C-terminal end of
      the residue

<400> SEQUENCE: 5

Xaa Leu Trp Arg Ala Leu Trp Arg Leu Leu Arg Ala Leu Trp Arg Leu
1               5                   10                  15

Leu Trp Lys Ala
            20

<210> SEQ ID NO 6
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Residue is acylated on the N-terminal end
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: Cysteamide is attached on the C-terminal end of
      the residue

<400> SEQUENCE: 6

Xaa Leu Trp Arg Ala Leu Trp Arg Leu Leu Arg Asn Leu Trp Arg Leu
1               5                   10                  15

Leu Trp Lys Ala
            20

<210> SEQ ID NO 7
<211> LENGTH: 19
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (12)..(12)
<223> OTHER INFORMATION: X = S or T
<220> FEATURE:
<221> NAME/KEY: MISC_FEATURE
<222> LOCATION: (19)..(19)
<223> OTHER INFORMATION: X = K or R

<400> SEQUENCE: 7

Xaa Leu Phe Arg Ala Leu Trp Arg Leu Leu Arg Xaa Leu Trp Arg Leu
1               5                   10                  15
```

Leu Trp Xaa

```
<210> SEQ ID NO 8
<211> LENGTH: 20
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (12)..(12)
<223> OTHER INFORMATION: X = S or T
<220> FEATURE:
<221> NAME/KEY: MISC_FEATURE
<222> LOCATION: (19)..(19)
<223> OTHER INFORMATION: X = K or R

<400> SEQUENCE: 8

Xaa Leu Trp Arg Ala Leu Trp Arg Leu Trp Arg Xaa Leu Trp Arg Leu
1               5                   10                  15

Leu Trp Xaa Ala
            20

<210> SEQ ID NO 9
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (10)..(10)
<223> OTHER INFORMATION: X = L, C or I
<220> FEATURE:
<221> NAME/KEY: MISC_FEATURE
<222> LOCATION: (12)..(12)
<223> OTHER INFORMATION: X = S or T
<220> FEATURE:
<221> NAME/KEY: MISC_FEATURE
<222> LOCATION: (19)..(19)
<223> OTHER INFORMATION: X = K or R

<400> SEQUENCE: 9

Xaa Leu Trp Arg Ala Leu Trp Arg Leu Xaa Arg Xaa Leu Trp Arg Leu
1               5                   10                  15

Trp Arg Xaa Ala
            20

<210> SEQ ID NO 10
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (12)..(12)
<223> OTHER INFORMATION: X = S or T
<220> FEATURE:
<221> NAME/KEY: MISC_FEATURE
```

-continued

```
<222> LOCATION: (19)..(19)
<223> OTHER INFORMATION: X = K or R

<400> SEQUENCE: 10

Xaa Leu Trp Arg Ala Leu Trp Arg Leu Trp Arg Xaa Leu Trp Arg Leu
1               5                   10                  15

Trp Arg Xaa Ala
            20

<210> SEQ ID NO 11
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (10)..(10)
<223> OTHER INFORMATION: X = L or I
<220> FEATURE:
<221> NAME/KEY: MISC_FEATURE
<222> LOCATION: (19)..(19)
<223> OTHER INFORMATION: X = K or R

<400> SEQUENCE: 11

Xaa Leu Trp Arg Ala Leu Trp Arg Leu Xaa Arg Ala Leu Trp Arg Leu
1               5                   10                  15

Leu Trp Xaa Ala
            20

<210> SEQ ID NO 12
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (10)..(10)
<223> OTHER INFORMATION: X = L, C or I
<220> FEATURE:
<221> NAME/KEY: MISC_FEATURE
<222> LOCATION: (19)..(19)
<223> OTHER INFORMATION: X = K or R

<400> SEQUENCE: 12

Xaa Leu Trp Arg Ala Leu Trp Arg Leu Xaa Arg Asn Leu Trp Arg Leu
1               5                   10                  15

Leu Trp Xaa Ala
            20

<210> SEQ ID NO 13
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
```

```
<221> NAME/KEY: MISC_FEATURE
<222> LOCATION: (3)..(3)
<223> OTHER INFORMATION: X = F or W
<220> FEATURE:
<221> NAME/KEY: MISC_FEATURE
<222> LOCATION: (10)..(10)
<223> OTHER INFORMATION: X = L, W, C or I
<220> FEATURE:
<221> NAME/KEY: MISC_FEATURE
<222> LOCATION: (12)..(12)
<223> OTHER INFORMATION: X = S, A, N or T
<220> FEATURE:
<221> NAME/KEY: MISC_FEATURE
<222> LOCATION: (17)..(17)
<223> OTHER INFORMATION: X = L or W
<220> FEATURE:
<221> NAME/KEY: MISC_FEATURE
<222> LOCATION: (18)..(18)
<223> OTHER INFORMATION: X = W or R
<220> FEATURE:
<221> NAME/KEY: MISC_FEATURE
<222> LOCATION: (19)..(19)
<223> OTHER INFORMATION: X = K or R
<220> FEATURE:
<221> NAME/KEY: MISC_FEATURE
<222> LOCATION: (20)..(20)
<223> OTHER INFORMATION: X = A or none

<400> SEQUENCE: 13

Xaa Leu Xaa Arg Ala Leu Trp Arg Leu Xaa Arg Xaa Leu Trp Arg Leu
1               5                   10                  15

Xaa Xaa Xaa Xaa
            20

<210> SEQ ID NO 14
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (3)..(3)
<223> OTHER INFORMATION: X = F or W
<220> FEATURE:
<221> NAME/KEY: MISC_FEATURE
<222> LOCATION: (10)..(10)
<223> OTHER INFORMATION: X = L or W
<220> FEATURE:
<221> NAME/KEY: MISC_FEATURE
<222> LOCATION: (12)..(12)
<223> OTHER INFORMATION: X = S, A or N
<220> FEATURE:
<221> NAME/KEY: MISC_FEATURE
<222> LOCATION: (17)..(17)
<223> OTHER INFORMATION: X = L or W
<220> FEATURE:
<221> NAME/KEY: MISC_FEATURE
<222> LOCATION: (18)..(18)
<223> OTHER INFORMATION: X = W or R
<220> FEATURE:
<221> NAME/KEY: MISC_FEATURE
<222> LOCATION: (20)..(20)
<223> OTHER INFORMATION: X = A or none

<400> SEQUENCE: 14

Xaa Leu Xaa Arg Ala Leu Trp Arg Leu Xaa Arg Xaa Leu Trp Arg Leu
1               5                   10                  15

Xaa Xaa Lys Xaa
            20
```

```
<210> SEQ ID NO 15
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Cholesterol, Pegylation, stearyl, palmitoyl,
      small FC or FAB fragments, nitrilotriacetic acid (2 x NTA), or
      brain targeting peptides may be attached
<220> FEATURE:
<221> NAME/KEY: MISC_FEATURE
<222> LOCATION: (19)..(19)
<223> OTHER INFORMATION: Cysteamide is attached on the C-terminal end of
      the residue

<400> SEQUENCE: 15

Ala Leu Phe Arg Ala Leu Trp Arg Leu Leu Arg Ser Leu Trp Arg Leu
1               5                   10                  15

Leu Trp Lys

<210> SEQ ID NO 16
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Residue is acylated on the N-terminal end
<220> FEATURE:
<221> NAME/KEY: MISC_FEATURE
<222> LOCATION: (19)..(19)
<223> OTHER INFORMATION: Cysteamide is attached on the C-terminal end of
      the residue
<220> FEATURE:
<221> NAME/KEY: MISC_FEATURE
<222> LOCATION: (19)..(19)
<223> OTHER INFORMATION: Cholesterol, Pegylation, stearyl, palmitoyl,
      small FC or FAB fragments, nitrilotriacetic acid (2 x NTA), or
      brain targeting peptides may be attached

<400> SEQUENCE: 16

Ala Leu Phe Arg Ala Leu Trp Arg Leu Leu Arg Ser Leu Trp Arg Leu
1               5                   10                  15

Leu Trp Lys

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 17
ggcgaagauc aacauggcat t                                            21

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 18
```
ugccauguug aucuucgccct t                                    21

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 19
ggugaagauc agcauggcat t                                     21

<210> SEQ ID NO 20
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 20
ugccaugucg aucuucaccct t                                    21

<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 21
caucaucccu gccucuacut t                                     21

<210> SEQ ID NO 22
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 22
aguagaggca gggaugaug                                        19

<210> SEQ ID NO 23
<211> LENGTH: 27
<212> TYPE: PRT
<213> ORGANISM: Artificial sequence
<220> FEATURE:
<223> OTHER INFORMATION: Synthetic peptide

<400> SEQUENCE: 23

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 24
<211> LENGTH: 21
<212> TYPE: PRT
<213> ORGANISM: Artificial sequence
<220> FEATURE:
<223> OTHER INFORMATION: Synthetic peptide

<400> SEQUENCE: 24

Lys Glu Thr Trp Trp Glu Thr Trp Trp Thr Glu Trp Ser Gln Pro Lys
1               5                   10                  15

```
<210> SEQ ID NO 25
<211> LENGTH: 20
<212> TYPE: PRT
<213> ORGANISM: Artificial sequence
<220> FEATURE:
<223> OTHER INFORMATION: Synthetic peptide

<400> SEQUENCE: 25

Gly Leu Phe Lys Ala Leu Leu Lys Leu Leu Lys Ser Leu Trp Lys Leu
1               5                   10                  15

Leu Leu Lys Ala
            20

<210> SEQ ID NO 26
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 26
uggcagugug guuagcuggu ug                                          22

<210> SEQ ID NO 27
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (8)..(8)
<223> OTHER INFORMATION: X = R, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X = S, which is linked to the R residue at
      position 8 by a hydrocarbon linkage

<400> SEQUENCE: 27

Xaa Leu Phe Arg Ala Leu Trp Xaa Leu Leu Arg Xaa Leu Trp Arg Leu
1               5                   10                  15

Leu Trp Lys

<210> SEQ ID NO 28
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (8)..(8)
<223> OTHER INFORMATION: X = R, which is linked to the S residue at
      position 12 by a hydrocarbon linkage
<220> FEATURE:
<221> NAME/KEY: MISC_FEATURE
<222> LOCATION: (12)..(12)
```

```
<223> OTHER INFORMATION: X = S, which is linked to the R residue at
      position 8 by a hydrocarbon linkage

<400> SEQUENCE: 28

Xaa Leu Phe Leu Ala Arg Trp Xaa Leu Leu Arg Xaa Leu Trp Arg Leu
1               5                   10                  15

Leu Trp Lys

<210> SEQ ID NO 29
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (8)..(8)
<223> OTHER INFORMATION: X = S, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X = S, which is linked to the S residue at
      position 8 by a hydrocarbon linkage

<400> SEQUENCE: 29

Xaa Leu Phe Arg Ala Leu Trp Xaa Leu Leu Arg Xaa Leu Trp Arg Leu
1               5                   10                  15

Leu Trp Lys

<210> SEQ ID NO 30
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (8)..(8)
<223> OTHER INFORMATION: X = S, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X = S, which is linked to the S residue at
      position 8 by a hydrocarbon linkage

<400> SEQUENCE: 30

Xaa Leu Phe Leu Ala Arg Trp Xaa Leu Leu Arg Xaa Leu Trp Arg Leu
1               5                   10                  15

Leu Trp Lys

<210> SEQ ID NO 31
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
```

```
<220> FEATURE:
<221> NAME/KEY: MISC_FEATURE
<222> LOCATION: (11)..(11)
<223> OTHER INFORMATION: X = R, which is linked to the S residue at
      position 15 by a hydrocarbon linkage
<220> FEATURE:
<221> NAME/KEY: MISC_FEATURE
<222> LOCATION: (15)..(15)
<223> OTHER INFORMATION: X = S, which is linked to the R residue at
      position 11 by a hydrocarbon linkage

<400> SEQUENCE: 31

Xaa Leu Phe Arg Ala Leu Trp Arg Leu Leu Xaa Ser Leu Trp Xaa Leu
1               5                   10                  15

Leu Trp Lys

<210> SEQ ID NO 32
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (11)..(11)
<223> OTHER INFORMATION: X = R, which is linked to the S residue at
      position 15 by a hydrocarbon linkage
<220> FEATURE:
<221> NAME/KEY: MISC_FEATURE
<222> LOCATION: (15)..(15)
<223> OTHER INFORMATION: X = S, which is linked to the R residue at
      position 11 by a hydrocarbon linkage

<400> SEQUENCE: 32

Xaa Leu Phe Leu Ala Arg Trp Arg Leu Leu Xaa Ser Leu Trp Xaa Leu
1               5                   10                  15

Leu Trp Lys

<210> SEQ ID NO 33
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (11)..(11)
<223> OTHER INFORMATION: X = S, which is linked to the S residue at
      position 15 by a hydrocarbon linkage
<220> FEATURE:
<221> NAME/KEY: MISC_FEATURE
<222> LOCATION: (15)..(15)
<223> OTHER INFORMATION: X = S, which is linked to the S residue at
      position 11 by a hydrocarbon linkage

<400> SEQUENCE: 33

Xaa Leu Phe Arg Ala Leu Trp Arg Leu Leu Xaa Ser Leu Trp Xaa Leu
1               5                   10                  15

Leu Trp Lys

<210> SEQ ID NO 34
<211> LENGTH: 19
```

```
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (11)..(11)
<223> OTHER INFORMATION: X = S, which is linked to the S residue at
      position 15 by a hydrocarbon linkage
<220> FEATURE:
<221> NAME/KEY: MISC_FEATURE
<222> LOCATION: (15)..(15)
<223> OTHER INFORMATION: X = S, which is linked to the S residue at
      position 11 by a hydrocarbon linkage

<400> SEQUENCE: 34

Xaa Leu Phe Leu Ala Arg Trp Arg Leu Leu Xaa Ser Leu Trp Xaa Leu
1               5                   10                  15

Leu Trp Lys

<210> SEQ ID NO 35
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (5)..(5)
<223> OTHER INFORMATION: X = R, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X = S, which is linked to the R residue at
      position 5 by a hydrocarbon linkage

<400> SEQUENCE: 35

Xaa Leu Phe Ala Xaa Leu Trp Arg Leu Leu Arg Xaa Leu Trp Arg Leu
1               5                   10                  15

Leu Trp Lys

<210> SEQ ID NO 36
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (3)..(3)
<223> OTHER INFORMATION: X = F or W
<220> FEATURE:
<221> NAME/KEY: MISC_FEATURE
<222> LOCATION: (8)..(8)
<223> OTHER INFORMATION: X = R or S
<220> FEATURE:
<221> NAME/KEY: MISC_FEATURE
<222> LOCATION: (10)..(10)
<223> OTHER INFORMATION: X = L, W, C or I
<220> FEATURE:
```

```
<221> NAME/KEY: MISC_FEATURE
<222> LOCATION: (11)..(11)
<223> OTHER INFORMATION: X = R or S
<220> FEATURE:
<221> NAME/KEY: MISC_FEATURE
<222> LOCATION: (12)..(12)
<223> OTHER INFORMATION: X = S, A, N or T
<220> FEATURE:
<221> NAME/KEY: MISC_FEATURE
<222> LOCATION: (15)..(15)
<223> OTHER INFORMATION: X = R or S
<220> FEATURE:
<221> NAME/KEY: MISC_FEATURE
<222> LOCATION: (17)..(17)
<223> OTHER INFORMATION: X = L or W
<220> FEATURE:
<221> NAME/KEY: MISC_FEATURE
<222> LOCATION: (18)..(18)
<223> OTHER INFORMATION: X = W or R
<220> FEATURE:
<221> NAME/KEY: MISC_FEATURE
<222> LOCATION: (19)..(19)
<223> OTHER INFORMATION: X = K or R
<220> FEATURE:
<221> NAME/KEY: MISC_FEATURE
<222> LOCATION: (20)..(20)
<223> OTHER INFORMATION: X = A or none

<400> SEQUENCE: 36

Xaa Leu Xaa Arg Ala Leu Trp Xaa Leu Xaa Xaa Xaa Leu Trp Xaa Leu
1               5                   10                  15

Xaa Xaa Xaa Xaa
            20

<210> SEQ ID NO 37
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (3)..(3)
<223> OTHER INFORMATION: X = F or W
<220> FEATURE:
<221> NAME/KEY: MISC_FEATURE
<222> LOCATION: (8)..(8)
<223> OTHER INFORMATION: X = R or S
<220> FEATURE:
<221> NAME/KEY: MISC_FEATURE
<222> LOCATION: (10)..(10)
<223> OTHER INFORMATION: X = L, W, C or I
<220> FEATURE:
<221> NAME/KEY: MISC_FEATURE
<222> LOCATION: (11)..(11)
<223> OTHER INFORMATION: X = R or S
<220> FEATURE:
<221> NAME/KEY: MISC_FEATURE
<222> LOCATION: (12)..(12)
<223> OTHER INFORMATION: X = S, A, N or T
<220> FEATURE:
<221> NAME/KEY: MISC_FEATURE
<222> LOCATION: (15)..(15)
<223> OTHER INFORMATION: X = R or S
<220> FEATURE:
<221> NAME/KEY: MISC_FEATURE
<222> LOCATION: (17)..(17)
<223> OTHER INFORMATION: X = L or W
<220> FEATURE:
<221> NAME/KEY: MISC_FEATURE
<222> LOCATION: (18)..(18)
<223> OTHER INFORMATION: X = W or R
```

```
<220> FEATURE:
<221> NAME/KEY: MISC_FEATURE
<222> LOCATION: (19)..(19)
<223> OTHER INFORMATION: X = K or R
<220> FEATURE:
<221> NAME/KEY: MISC_FEATURE
<222> LOCATION: (20)..(20)
<223> OTHER INFORMATION: X = A or none

<400> SEQUENCE: 37

Xaa Leu Xaa Leu Ala Arg Trp Xaa Leu Xaa Xaa Xaa Leu Trp Xaa Leu
1               5                   10                  15

Xaa Xaa Xaa Xaa
            20

<210> SEQ ID NO 38
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (3)..(3)
<223> OTHER INFORMATION: X = F or W
<220> FEATURE:
<221> NAME/KEY: MISC_FEATURE
<222> LOCATION: (8)..(8)
<223> OTHER INFORMATION: X = R or S
<220> FEATURE:
<221> NAME/KEY: MISC_FEATURE
<222> LOCATION: (10)..(10)
<223> OTHER INFORMATION: X = L, W, C or I
<220> FEATURE:
<221> NAME/KEY: MISC_FEATURE
<222> LOCATION: (11)..(11)
<223> OTHER INFORMATION: X = R or S
<220> FEATURE:
<221> NAME/KEY: MISC_FEATURE
<222> LOCATION: (12)..(12)
<223> OTHER INFORMATION: X = S, A, N or T
<220> FEATURE:
<221> NAME/KEY: MISC_FEATURE
<222> LOCATION: (15)..(15)
<223> OTHER INFORMATION: X = R or S
<220> FEATURE:
<221> NAME/KEY: MISC_FEATURE
<222> LOCATION: (17)..(17)
<223> OTHER INFORMATION: X = L or W
<220> FEATURE:
<221> NAME/KEY: MISC_FEATURE
<222> LOCATION: (18)..(18)
<223> OTHER INFORMATION: X = W or R
<220> FEATURE:
<221> NAME/KEY: MISC_FEATURE
<222> LOCATION: (19)..(19)
<223> OTHER INFORMATION: X = K or R
<220> FEATURE:
<221> NAME/KEY: MISC_FEATURE
<222> LOCATION: (20)..(20)
<223> OTHER INFORMATION: X = A or none

<400> SEQUENCE: 38

Xaa Leu Xaa Ala Arg Leu Trp Xaa Leu Xaa Xaa Xaa Leu Trp Xaa Leu
1               5                   10                  15

Xaa Xaa Xaa Xaa
            20
```

US 9,376,468 B2

CELL PENETRATING PEPTIDES FOR INTRACELLULAR DELIVERY OF MOLECULES

SEQUENCE LISTING SUBMISSION VIA EFS-WEB

A computer readable text file, entitled "045636-5239_SequenceListing.txt" created on or about 2 Oct. 2013, with a file size of about 20 kb contains the sequence listing for this application and is hereby incorporated by reference in its entirety.

The present invention pertains to the field of intracellular delivery of molecules such as nucleic acids and small hydrophobic molecules. In particular, the invention relates to a new cell-penetrating peptide (CPP) family, which exhibits high efficacy, low toxicity and a natural tropism for lung tissues.

Although small molecules remain the major drugs used in clinic, in numerous cases, their therapeutic impact has reached limitations such as insufficient capability to reach targets, lack of specificity, requirement for high doses leading to toxicity and major side effects. Over the past ten years, in order to circumvent limitations of small molecules and of gene-based therapies, we have witnessed a dramatic acceleration in the discovery of larger therapeutic molecules such as proteins, peptides and nucleic acids which present a high specificity for their target but do not follow Lipinski's rules. Pharmaceutical potency of these molecules remains restricted by their poor stability in vivo and by their low uptake in cells. Therefore, "delivery" has become a central piece of the therapeutic puzzle and new milestones have been established to validate delivery strategies: (a) lack of toxicity, (b) efficiency at low doses in vivo, (c) easy to handle for therapeutic applications (d) rapid endosomal release and (e) ability to reach the target. Although viral delivery strategies had given much hope for gene and cellular therapies, their clinical application has suffered from side- and toxicity-effects [1,2]. Researches were mainly focused on the development of non-viral strategies, and different methods have been proposed including lipid, polycationic nanoparticles and peptide-based formulations, but only few of these technologies have been efficient in vivo and have reached the clinic. Cell Penetrating Peptides (CPP) are one of the most promising non-viral strategies. Although definition of CPPs is constantly evolving, they are generally described as short peptides of less than 30 amino acids either derived from proteins or from chimeric sequences. They are usually amphipathic and possess a net positive charge [3-5]. CPPs are able to penetrate biological membranes, to trigger the movement of various biomolecules across cell membranes into the cytoplasm and to improve their intracellular routing, thereby facilitating interactions with the target. CPPs can be subdivided into two main classes, the first requiring chemical linkage with the cargo and the second involving the formation of stable, non-covalent complexes. CPPs from both strategies have been reported to favour the delivery of a large panel of cargos (plasmid DNA, oligonucleotide, siRNA, PNA, protein, peptide, liposome, nanoparticle . . . ) into a wide variety of cell types and in vivo models [3-7].

Twenty years ago, the concept of protein transduction domain (PTD) was proposed based on the observation that some proteins, mainly transcription factors, could shuttle within cells and from one cell to another [for review see ref 3,4]. The first observation was made in 1988, by Frankel and Pabo. They showed that the transcription-transactivating (Tat) protein of HIV-1 could enter cells and translocate into the nucleus. In 1991, the group of Prochiantz reached the same conclusions with the Drosophila Antennapedia homeodomain and demonstrated that this domain was internalized by neuronal cells. These works were at the origin of the discovery in 1994 of the first Protein Transduction Domain: a 16 mer-peptide derived from the third helix of the homeodomain of Antennapedia named Penetratin. In 1997, the group of Lebleu identified the minimal sequence of Tat required for cellular uptake and the first proofs-of-concept of the application of PTD in vivo, were reported by the group of Dowdy, for the delivery of small peptides and large proteins. Historically, the notion of Cell Penetrating Peptide (CPP) was introduced by the group of Langel, in 1998, with the design of the first chimeric peptide carrier, the Transportan, which derived from the N-terminal fragment of the neuropeptide galanin, linked to mastoparan, a wasp venom peptide. Transportan has been originally reported to improve the delivery of PNAs both in cultured cells and in vivo. In 1997, the group of Heitz and Divita proposed a new strategy involving CPP in the formation of stable but non-covalent complexes with their cargo [7]. The strategy was first based on the short peptide carrier (MPG) consisting of two domains: a hydrophilic (polar) domain and a hydrophobic (apolar) domain. MPG was designed for the delivery of nucleic acids [7]. The primary amphipathic peptide Pep-1 was then proposed for non-covalent delivery of proteins and peptides [8]. Then the groups of Wender and of Futaki demonstrated that polyarginine sequences (Arg8) are sufficient to drive small and large molecules into cells and in vivo. Ever since, many CPPs derived from natural or unnatural sequences have been identified and the list is constantly increasing. Peptides have been derived from VP22 protein of Herpes Simplex Virus, from calcitonin, from antimicrobial or toxin peptides, from proteins involved in cell cycle regulation, as well as from polyproline-rich peptides [reviews 4-6].

The inventors have now designed a new family of cell-penetrating peptides for the delivery of charged and hydrophobic molecules, named VEPEP-6. Delivery strategies using VEPEP-6 peptides as the outer layer of nanoparticles are referred to as NANOPEP-6.

VEPEP-6 are short secondary amphipathic peptides forming stable nanoparticles with molecules such as nucleic-acids (in particular siRNA), DNA mimic and small hydrophobic molecules, hereafter designated as "SHM". VEPEP-6 vectors comprise the following amino acid sequence:

$X_1LX_2RALWX_9LX_3X_9X_4LWX_9LX_5X_6X_7X_8$ (SEQ ID No: 36), or $X_1LX_2LARWX_9LX_3X_9X_4LWX_9LX_5X_6X_7X_8$ (SEQ ID No: 37), or $X_1LX_2ARLWX_9LX_3X_9X_4LWX_9LX_5X_6X_7X_8$ (SEQ ID No: 38), wherein $X_1$ is beta-A or S,
$X_2$ is F or W,
$X_3$ is L, W, C or I,
$X_4$ is S, A, N or T,
$X_5$ is L or W,
$X_6$ is W or R,
$X_7$ is K or R,
$X_8$ is A or none, and
$X_9$ is R or S.

According to a particular embodiment, VEPEP-6 vectors comprise the following amino acid sequence:

(SEQ ID No: 13)
$X_1LX_2RALWRLX_3RX_4LWRLX_5X_6X_7X_8$, wherein $X_1$ to $X_8$ are as described above.

VEPEP-6 strategy improves both ex-vivo and in vivo delivery and efficiency of nucleic acids and small hydrophobic molecules, without activating the innate immune response or inducing toxic side effects.

Other particular cell-penetrating peptides according to the present invention comprise the following amino acid sequence:

$X_1LX_2RALWRLX_3RX_4LWRLX_5X_6KX_7$, (SEQ ID No: 14)

wherein $X_1$ is beta-A or S, $X_2$ is F or W, $X_3$ is L or W, $X_4$ is S, A or N, $X_5$ is L or W, $X_6$ is W or R, $X_7$ is A or none.

According to a preferred embodiment of the present invention, illustrated in the experimental part below, the amino acid sequence of the cell-penetrating peptide is selected in the group consisting of:

$X_1LFRALWRLLRX_2LWRLLWX_3$ (SEQ ID No: 7)

$X_1LWRALWRLWRX_2LWRLLWX_3A$ (SEQ ID No: 8)

$X_1LWRALWRLX_4RX_2LWRLWRX_3A$ (SEQ ID No: 9)

$X_1LWRALWRLWRX_2LWRLWRX_3A$ (SEQ ID No: 10)

$X_1LWRALWRLX_5RALWRLLWX_3A$ (SEQ ID No: 11)
and $X_1LWRALWRLX_4RNLWRLLWX_3A$, (SEQ ID No: 12)

wherein $X_1$ is beta-A or S, $X_2$ is S or T, $X_3$ is K or R, $X_4$ is L, C or I and $X_5$ is L or I.

According to a preferred embodiment, a cell-penetrating peptide of the present invention further comprises, covalently linked to the N-terminal end of the amino acid sequence, one or several chemical entities selected in the group consisting of an acetyl, a fatty acid, a cholesterol, a poly-ethylene glycol, a nuclear localization signal, a nuclear export signal, an antibody, a polysaccharide and a targeting molecule.

In addition or alternatively, a cell-penetrating peptide according to the invention can comprise, covalently linked to the C-terminal end of its amino acid sequence, one or several groups selected in the group consisting of a cysteamide, a cysteine, a thiol, an amide, a nitrilotriacetic acid (NTA) optionally substituted, a carboxyl, a linear or ramified $C_1$-$C_6$ alkyl optionally substituted, a primary or secondary amine, an osidic derivative, a lipid, a phospholipid, a fatty acid, a cholesterol, a poly-ethylene glycol, a nuclear localization signal, nuclear export signal, an antibody, a polysaccharide and a targeting molecule.

Particular examples of cell-penetrating peptides according to the invention are the following:

VEPEP-6a: (SEQ ID No: 1)
Ac-$X_1$LFRALWRLLRSLWRLLWK-cysteamide

VEPEP-6b: (SEQ ID No: 2)
Ac-$X_1$LWRALWRLWRSLWRLLWKA-cysteamide

VEPEP-6c: (SEQ ID No: 3)
Ac-$X_1$LWRALWRLLRSLWRLWRKA-cysteamide

VEPEP-6d: (SEQ ID No: 4)
Ac-$X_1$LWRALWRLWRSLWRLWRKA-cysteamide

VEPEP-6e: (SEQ ID No: 5)
Ac-$X_1$LWRALWRLLRALWRLLWKA-cysteamide
and

VEPEP-6f: (SEQ ID No: 6)
Ac-$X_1$LWRALWRLLRNLWRLLWKA-cysteamide, wherein $X_1$ is beta-A or S, and Ac represents an acetyl.

According to a particular embodiment of the present invention, the VEPEP-6 cell-penetrating peptide is stapled, which means that it comprises a chemical linkage (in addition to the amino acid chain) between two residues. In a preferred embodiment of stapled VEPEP-6 peptides (noted ST-VEPEP-6), the VEPEP-6 peptide comprises a hydrocarbon linkage between two residues which are separated by three or six residues. The skilled artisan can obtain these peptides by using techniques which are available in the art, for example as described by Verdine and Hilinski, Methods in Enzymology, 2012 [1,7].

In cell penetrating peptides with an amino acid sequence consisting of SEQ ID No: 36, 37 or 38, the hydrocarbon linkage preferably links the residues at positions 8 and 12, or the residues at positions 11 and 15, or the residues at positions 8 and 15. In this later configuration (linkage between residues 8 and 15), the residue in position 8 is R.

Non-limitative examples of stapled VEPEP-6 according to the invention are as follows:

ST-VEPEP-6a: (SEQ ID No: 27)
Ac-$X_1$LFRALWR$_S$LLRS$_S$LWRLLWK-cysteamide

ST-VEPEP-6aa: (SEQ ID No: 28)
Ac-$X_1$LFLARWR$_S$LLRS$_S$LWRLLWK-cysteamide

ST-VEPEP-6ab: (SEQ ID No: 29)
Ac-$X_1$LFRALWS$_S$LLRS$_S$LWRLLWK-cysteamide

ST-VEPEP-6ad: (SEQ ID No: 30)
Ac-$X_1$LFLARWS$_S$LLRS$_S$LWRLLWK-cysteamide

ST-VEPEP-6b: (SEQ ID No: 31)
Ac-$X_1$LFRALWRLLR$_S$SLWS$_S$LLWK-cysteamide

ST-VEPEP-6ba: (SEQ ID No: 32)
Ac-$X_1$LFLARWRLLR$_S$SLWS$_S$LLWK-cysteamide

ST-VEPEP-6bb: (SEQ ID No: 33)
Ac-$X_1$LFRALWRLLS$_S$SLWS$_S$LLWK-cysteamide

ST-VEPEP-6bd: (SEQ ID No: 34)
Ac-$X_1$LFLARWRLLS$_S$SLWS$_S$LLWK-cysteamide

ST-VEPEP-6c: (SEQ ID No: 35)
Ac-$X_1$LFAR$_S$LWRLLRS$_S$LWRLLWK-cysteamide, wherein $X_1$ is beta-A or S and wherein the residues followed by an inferior "s" are those which are linked by said hydrocarbon linkage.

Another aspect of the present invention is a complex comprising a cell-penetrating peptide as described above and a cargo selected amongst nucleic acids and hydrophobic molecules. Examples of nucleic acid cargoes are small single stranded RNA or DNA (size between 2 to 40 bases) and double stranded RNA or DNA (size up to 100 base pairs), in particular siRNA selected to silence a target mRNA. As disclosed in Example 7 below, the cell-penetrating peptides according to the invention can be used to deliver a mix of several different siRNA, with an improved inhibiting activity. As illustrated in example 8 below, other advantageous nucleic acid cargos in the complexes according to the invention are microRNAs (miRNAs), selected for their ability to affect expression of genes and proteins that regulate cell proliferation and/or cell death. In another preferred embodiment of the complex according to the invention, the cargo is a small molecule (size lower that 1.5 kDa), preferably hydrophobic. Non-limitative examples of small hydrophobic molecules which can be used include daunomycin, Paclitaxel, doxorubicin, AZT, porphyrin, fluorescently-labelled-nucleosides or nucleotides (FAM-Guanosine), hydrophobic maghemite (contrast agents or magnetic nanoparticles $Fe_2O_3$) and fluorescent dyes.

The size of the complexes described above is preferably between 50 and 300 nm, more preferably between 50 and 200 nm (the size of the complex herein designates its mean diameter).

In the complexes according to the invention, the VEPEP-6/cargo molar ratio depends on the nature and size of the cargo, but is generally comprised between 1/1 and 50/1. For siRNA cargoes, the cargo/VEPEP-6 molar ratio preferably ranges from 10/1 to 30/1, more preferably from 15/1 to 25/1.

According to an advantageous embodiment of the complexes as described above, the VEPEP-6 peptides comprise an acetyl group covalently linked to their N-terminus, and/or a cysteamide group covalently linked to their C-terminus.

The above complexes can be advantageously used as "core shells" for obtaining bigger complexes, or nanoparticles, by an additional step of coating the VEPEP-6/cargo complex with another layer of cell-penetrating peptides, which can be different from the VEPEP-6 peptides described above. Examples of such nanoparticles are CADY/VEPEP-6/siRNA and MPG/VEPEP-6/siRNA nanoparticles described in example 5.4. Other examples of peptides which can be used for forming nanoparticles by coating a VEPEP-6/cargo complex are PEP-1, ppTG1 and polyarginine such as Arg8.

Another aspect of the present invention pertains to nanoparticles made of a "core shell" comprising a cargo and a first carrier molecule, surrounded by VEPEP-6 peptides. These are herein referred to as "NANOPEP-6" particles. NANOPEP-6 technology constitutes a "custom-built" delivery system containing a common core particle, trapping therapeutic molecule, with surface VEPEP-6 peptides which are preferably functionalized for tumour or tissue targeting in vivo. From a structural point of view, NANOPEP-6 particles are constituted by a "core" which is coated by a layer of VEPEP-6 peptides. The "core" corresponds to a complex comprising a cargo and a vector or carrier such as a first cell-penetrating peptide, a liposome, a polycationic structure, a carbon nanoparticle, etc. In NANOPEP-6 particles, the layer of VEPEP-6 peptides (peripheral peptide) stabilizes the particle and can be functionalized. Functionalizing NANOPEP-6 particle surface with either cholesterol or PEG-molecules improves particles stability in vivo, favours their administration by either systemic or topical route and allows rapid liberation of active cargoes within tumor cells or tissues. Functionalization of the surface of NANOPEP-6 particles with small Fab fragments, peptides, antibodies and lipids has been shown to favour in vivo tissue or tumor targeting (examples 5.2 and 5.3 below).

NANOPEP-6 technology improves both cellular and in vivo delivery of biologically active cargoes and has been validated on a large set of cell lines including adherent and suspension cell lines, hard to transfect cell lines. NANOPEP-6 particles strongly interact with cell membranes and enter the cell independently of the endosomal pathway or rapidly escape from early endosomes. NANOPEP-6 technology presents several advantages including rapid delivery with very high efficacy, stability in physiological buffers, lack of toxicity and of sensitivity to serum, ability of forming mix nanoparticles, can be functionalized and have been successfully applied to the delivery of different types of cargoes into a large variety of cell lines as well as in animal models, thereby constituting powerful tools for basic research and therapeutic applications. NANOPEP-6 technology can be applied both at therapeutic and diagnostic/theragnostic levels.

In a particular embodiment of NANOPEP-6 particles according to the present invention, the cargo is complexed to a first cell-penetrating peptide, which can be, for example, selected amongst CADY (described in U.S. Pat. No. 7,579, 318, herein incorporated by reference), MPG (SEQ ID No: 23, N-acetyl-GALFLGFLGAAGSTMGAWSQPKKKRKV-Cysteamide) or its variants described in U.S. Pat. No. 7,514, 530, PEP-1 (SEQ ID No: 24, N-acetyl-KETWWETWW-TEWSQPKKKRKV-cysteamide), PPTG1 (SEQ ID No: 25, GLFKALLKLLKSLWKLLLKA), poly Arginine motif such as Arg8, VEPEP-6 peptides described above, or any other known CPP. This cargo/CPP complex is then coated with a layer of VEPEP-6 peptides. According to this embodiment, the skilled artisan will advantageously choose the first CPP depending on the nature of the cargo, so that the complex of cargo and first CPP is stable. Hence, a wide diversity of cargoes can be included in NANOPEP-6 particles (See example: 5.3 using PEP-1/peptide complex associated to VEPEP-6, as short peptide are not cargo of VEPEP-6 peptide).

In the nanoparticles as above-described, the VEPEP-6/core molar ratio depends on the nature and size of the core, but is generally comprised between 1/1 and 50/1. For CPP/siRNA cores, the peripheral VEPEP-6/cargo molar ratio preferably ranges from 10/1 to 30/1, more preferably from 15/1 to 25/1. In what follows, when a ratio of peripheral peptide/core shell particle is indicated for nanoparticles according to the invention, this ratio in fact represents the peripheral peptide/cargo molar ratio.

In a preferred embodiment of the nanoparticles according to the invention, the size of the nanoparticle is between 80 and 400 nm.

According to an advantageous embodiment of the NANOPEP-6 particles according to the invention, the VEPEP-6 peptides forming the peripheral layer of the nanoparticles comprise an acetyl group covalently linked to their N-terminus, and/or a cysteamide group covalently linked to their C-terminus.

According to another preferred embodiment, described in example 4 and illustrated in Example 5.2 below, the core shell of the particles is coated with a VEPEP-6 peptide functionalized with NTA (for example, a VEPEP-6 peptide with nitrilotriacetic acid covalently linked to its C-terminus). This allows the subsequent attachment to the surface of the particle, of any protein (or other molecule) harboring a histidine tag. This strategy offers the major advantage of having a common two-layers particles "NANOPEP-6-HIS" that can be associated to any His-tagged molecule.

In the present text, the following notations will be used to describe the nanoparticles according to the present invention:

As already described, "NANOPEP-6" designates a particle comprising a core shell made of at least a cargo and a first carrier molecule, surrounded by a VEPEP-6 layer. To further specify the nature of the core shell carrier and of the cargo, the notation "NANOPEP-6/core shell carrier/cargo" notation will be used. For example, the nanoparticles formed by CADY/siRNA particles surrounded by a layer of VEPEP-6 peptides (Example 5.3 below) will be noted "NANOPEP-6/CADY/siRNA". In order to simplify the notations, nanoparticles formed with two layers of VEPEP-6 peptides around a cargo can be noted "NANOPEP-6/cargo".

The same principles are used to designate the functionalized nanoparticles, with the specificity that NTA-functionalized NANOPEP particles are noted NANOPEPHIS. Hence, in Example 5.2.2, "NANOPEP-6-HIS/PEP1/PC4" designates nanoparticles in which the PC4 cargo is complexed to PEP1 as first cell-penetrating peptide and then surrounded by a layer of NTA-functionalized VEPEP-6 peptides, and, in example 5.2.1, "MUC-NANOPEP-6-HIS/siRNA" designates nanoparticles with siRNA as a cargo, complexed to a first layer of VEPEP-6 peptides, and surrounded by a second layer of VEPEP-6 peptides which are functionalized and bound to a molecule targeting MUC1.

In particular embodiments of the complexes and nanoparticles according to the invention, at least part of the VEPEP-6 cell-penetrating peptides are bound to a targeting molecule. In the case of NANOPEP-6 particles, at least part of the cell-penetrating peptides which are at the periphery of the nanoparticle are preferentially bound to a targeting molecule. Examples of targeting molecules include: antibodies, Fc and FAB fragments, and ligands, especially targeting receptors which are over-expressed at the surface of certain cell-types, etc. Among the numerous molecules which can be targeted by antibodies, Fc and Fab fragments, one can cite the receptor tyrosine kinase HEK2 receptor, MUC1, the EGF receptor and CXCR4. Non-limitative examples of other ligands which can be used are: RGD-peptide, homing targeting peptides (brain NT1 peptide, Ganglion GM peptide), folic acid, polysaccharides, Matrix metalloprotease targeting peptide motif (MMP-9).

According to a particular embodiment of the present invention, the complexes or nanoparticles are formulated se that they can be stored during several months without losing their stability and functional efficacy. As disclosed in example 6 below, the complexes and nanoparticles of the invention can advantageously be lyophilized in the presence of a sugar. Non-limitative examples of sugars which can be used to that aim are sucrose, glucose and a mix thereof, and they can be used, for example, in a concentration ranging from 5% to 20%, preferably 5% to 10%, it being understood that a concentration of 5% is obtained by adding 5 μgrams per liter of solution before lyophilization.

Another aspect of the present invention is a therapeutic composition comprising a complex or a nanoparticle as described above. For example, a composition comprising a complex or nanoparticle having an anti-cyclin B1 siRNA as a cargo, and a targeting molecule specific for tumor cells (for example: RGD-peptide, folic acid, MUC-1 or HEK2 receptor antibodies . . . ), is part of the present invention. It is to be noted that complexes and nanoparticles according to the invention can also be advantageously used for formulating non-therapeutic compositions (for example, for research, imaging and/or diagnosis purposes).

Compositions according to the invention (therapeutic or non-therapeutic) can be formulated, for example, for intravenous, topical, intrarectal, intratumoral, intranasal or intradermal administration, as well as for administration via a mouth spray. Due to their specifically efficient delivery to the lung, particular compositions according to the present invention can target lung cells, for example for treating or diagnosing lung cancers or for treating lung diseases such as asthma. Any formulation known in the pharmacologic field can be used, such as suppository, solutions, sprays, ointments, etc. Of course, another object of the present invention is a method for delivering a molecule to a patient in need thereof, comprising administrating to said patient a complex or nanoparticle according to the present invention, in particular through intrarectal, intranasal (or oral, with a spray) or intradermal routes.

The present invention also pertains to a method for delivering a molecule into a cell in vitro, comprising a step of putting said cell into contact with a complex comprising said molecule and VEPEP-6 cell-penetrating peptides as described above.

The invention is further illustrated by the following figures and examples.

LEGENDS TO THE FIGURES

FIG. 1: Structure of VEPEP-6 in the presence of double stranded oligonucleotide or phospholipid as monitored by circular dichroism (a) and molecular modeling calculation (using Peplook program, ref 9) or NMR measurement (b).

Figure 2:
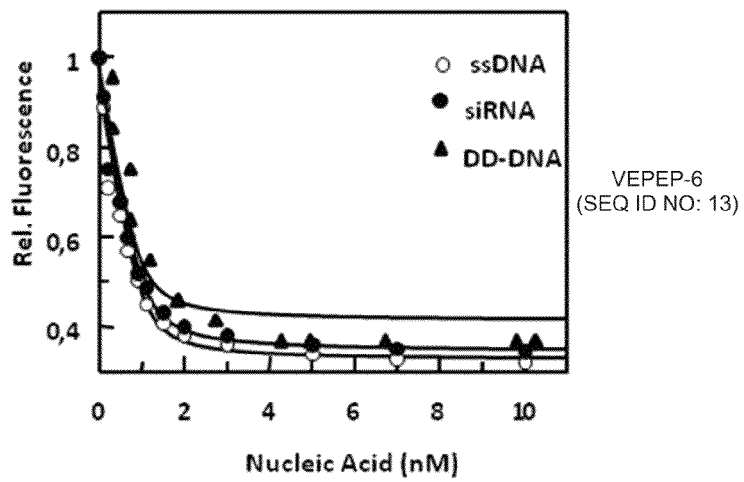

FIG. 2: Binding of nucleic acid to VEPEP-6a as monitored by TRP-intrinsic fluorescence spectroscopy. Dissociation constants were calculated from data fitting. Nucleic acids used: double stranded DNA (45/35 mer), siRNA (19/19 or 25/25) and single stranded DNA (19 or 36 mer)

Figure 3:
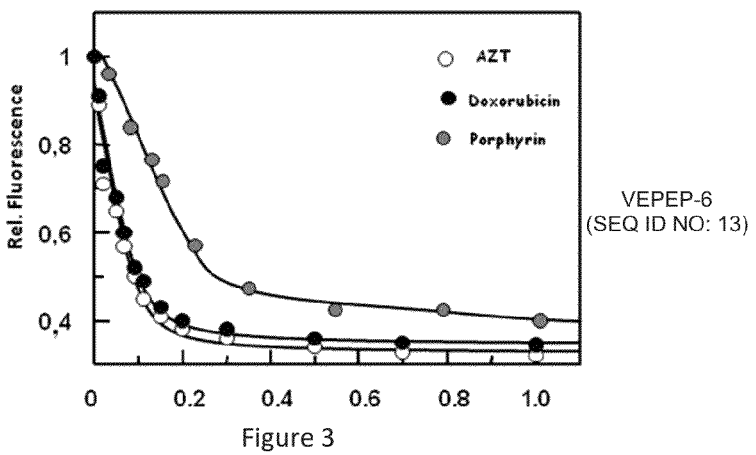

FIG. 3: Binding of small hydrophobic molecules to VEPEP-6 as monitored by fluorescence spectroscopy. The binding of Doxorubicin, AZT and Porphyrin to VEPEP-6 was monitored by following the quenching of tryptophan-intrinsic VEPEP-6 fluorescence and that of fluoresceine-labelled-Guanosine (FAM-G) by monitoring FAM-fluorescence. Dissociation constants were calculated from data fitting.

FIG. 4: Impact of VEPEP-6 particle size on silencing efficacy. A fixed concentration of 20 nM of siRNA (Cyc-B1) was associated with different molar ratios of VEPEP-6/siRNA ranging from 1/1 to 50/1. The size of the VEPEP-6/siRNA particles were measured by light scattering (grey bars) and the biological response associated with siRNA internalization was evaluated in cultured cells by measuring reduction of cyclin B1 protein levels 24 hrs after transfection (black bars).

FIG. 5: Structural analysis of VEPEP-6/siRNA complexes by scanning electron microscopy (a) and Atomic Force Microscopy (AFM) (b).

Figure 6:
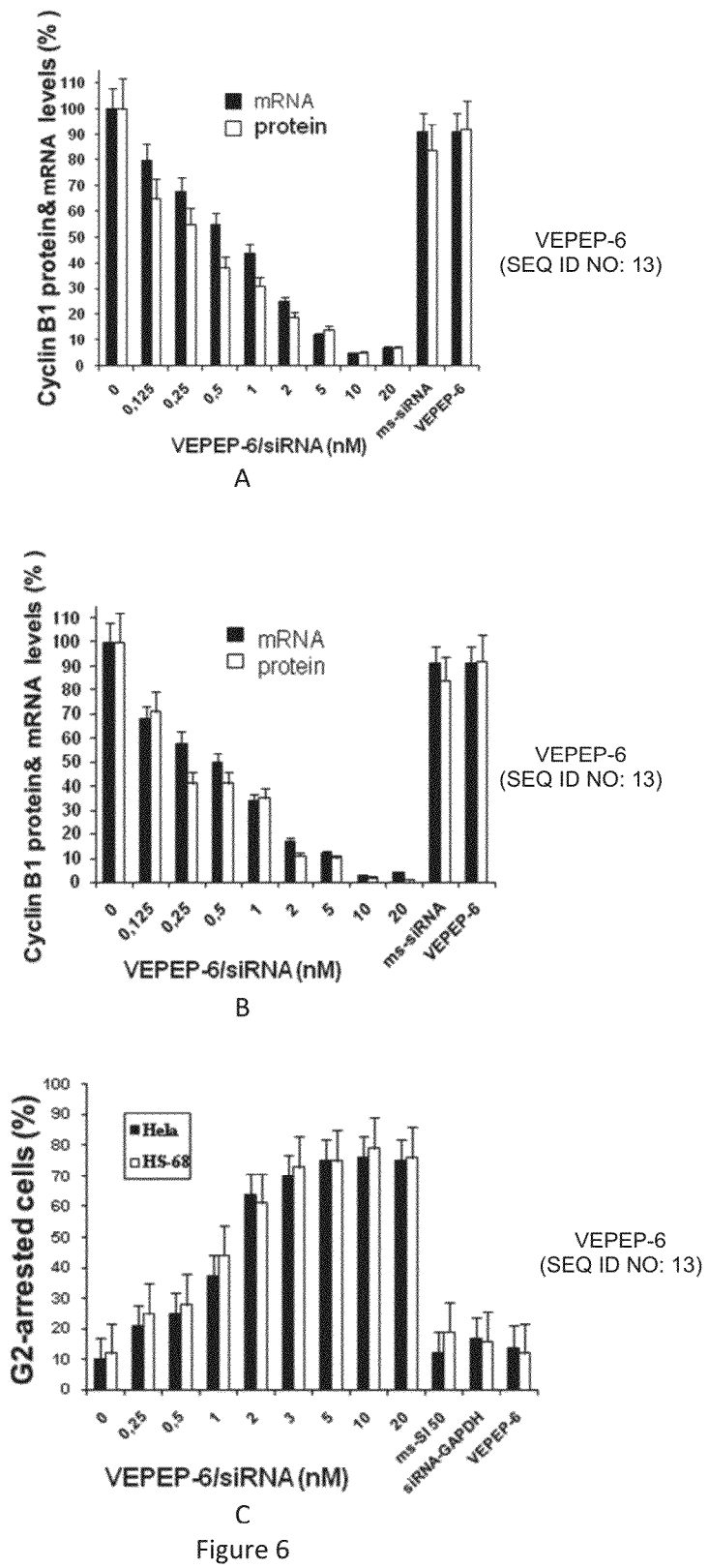

FIG. 6: VEPEP-6 dose response of Cyclin B1 silencing at the protein and mRNA levels on Hela (panel A) and HS68 (panel B) cells. Stock solution of VEPEP-6/siRNA (100 nM) particles were prepared at a molar ratio of 1/20 (siRNA/VEPEP-6), and lower concentrations (from 200 nM to 0.125 nM) were obtained by serial dilution of the stock solution in PBS. HeLa (Panel A) and HS-68 (Panel B) cells (60% confluency) were overlaid with preformed complexes for 30 min, then fresh DMEM supplemented with 10% FCS was added directly to the cells, which were then returned to the incubator for 24 hrs. Cyclin B1 protein levels were determined by Western Blotting using Cdk2 as a control for quantification (white bars). Cyclin B1 mRNA levels were measured 12 hrs after transfection using Quantigen technology (black bars).

Mismatched Cyc-B3 siRNA associated with VEPEP-6 (200 nM) and empty VEPEP-6 particles (20 μM) were used as a control. Panel C: Dose-response of G2-arrest associated with Cyclin B1 silencing. HeLa (black bars) and HS68 (white bars) cells were treated with increasing concentrations of VEPEP-6/siRNA-Cyc-B1 from 0.25 nM to 20 nM. The cell cycle status was evaluated by FACS analysis. Mismatched Cyc-B3 siRNA (100 nM) and GAPDH siRNA (100 nM) associated to VEPEP-6 as well as VEPEP-6 carrier alone (20 μM) were used as controls. Results are the means± of 4 separate experiments.

FIG. 7: Toxicity of VEPEP-6 particles: (A) The toxicity of VEPEP-6 particles was investigated by MTT assay (grey bars) and by monitoring the level of cyclophilin mRNA measured by Quantigen™ technology (Affymetrix) (white bars). HeLa cells were treated with increasing concentrations of VEPEP-6/siRNA particles ranging from 1 to 100 μM and toxicity was then evaluated 12 hr (Cyclophilin mRNA) or 24 hr (MTT) after treatment. (B) VEPEP-6 particle does not induce non-specific immune or interferon responses in vivo. VEPEP-6/siRNA (set 2), NANOPEP-6/siRNA (set 3) (1 mg/kg of siRNA), and VEPEP-6 carrier (Set 4) were intravenously injected into mice and cytokines induction were measured in the serum 6 (set A), 12 (set B), 24 (set C) and 48 (set D) hrs after injection using 10 plex Invitrogen kit (LMC 10001). This kit allowed the simultaneous measurement of mouse IL-1β, IL-2, IL-4, IL-5, IL-6, IL-10, IL-12, IFN-gamma, TNF-α, and GM-CSF in serum, or tissue culture supernatant. Data were compared to control molecule LPS (set 1). Reported data are the average of 3 separate experiments.

FIG. 8: (A) Binding of small hydrophobic fluorescent molecules (SFM) to VEPEP-6 as monitored by fluorescence spectroscopy. In the present case, a fluorescently labeled nucleotide (fluorescein-labeled-Guanine) was used. Dissociation constants were calculated from data fitting. (B) Effect of VEPEP-6 mediated doxorubicin on cancer cell viability. Dose responses of free (white bars) and VEPEP-6 mediated (grey bars) doxorubicin have been evaluated on the viability of U2OS and MCF7 cancer cells.

FIG. 9: VEPEP-6 mediated in cellulo delivery of SFM. A dose response of VEPEP-6 mediated SFM delivery was evaluated on Hela cell line. Membranes were labeled in green with WGA, nucleus in blue with Hoescht and SFM (fluorescein-labelled guanine) molecules are reported in red. The measurements were performed after 20 and 135 min incubation.

FIG. 10: Protocol of particle formation using VEPEP-6 (panel A) and functionalized-VEPEP-6 or NANOPEPHIS-6 (Panel B).

FIG. 11: NANOPEP-6 Cyclin B1 siRNA delivery upon topical and systemic injection. Athymic female nude mice were subcutaneously inoculated into the flank with 1×10$^6$ PC3 (panels A&B) or HT29 (panels C&D). Two to three weeks after tumour implant, when tumour size reached about 100 mm$^3$, animals were treated by intratumoral (panels A&C) injections, every 3 days, with a solution either saline buffer solution (closed triangle), free Cyc-B1 siRNA (open triangle), control siRNA Cyc-B3 (closed box) or Cyc-B1 siRNA at 5 μg (open circle) and 10 μg (closed circle) complexed with NANOPEP-6 at a 1/20 molar ratio. By intravenous (panels B&D) injections, every 3 days, with a solution either free Cyc-B1 siRNA (closed triangle), control siRNA Cyc-B3 (open triangle) or Cyc-B1 siRNA at 5 μg (open circle) and 10 μg (closed circle) complexed with NANOPEP-6 at a 1/20 molar ratio. Tumour diameter was measured in two directions at regular intervals using a digital calliper and tumour volume was calculated as length×width× height×0.52. Curves show the mean value of tumour size in a cohort of six animals and neither animal death nor any sign of toxicity were observed.

Figure 12:
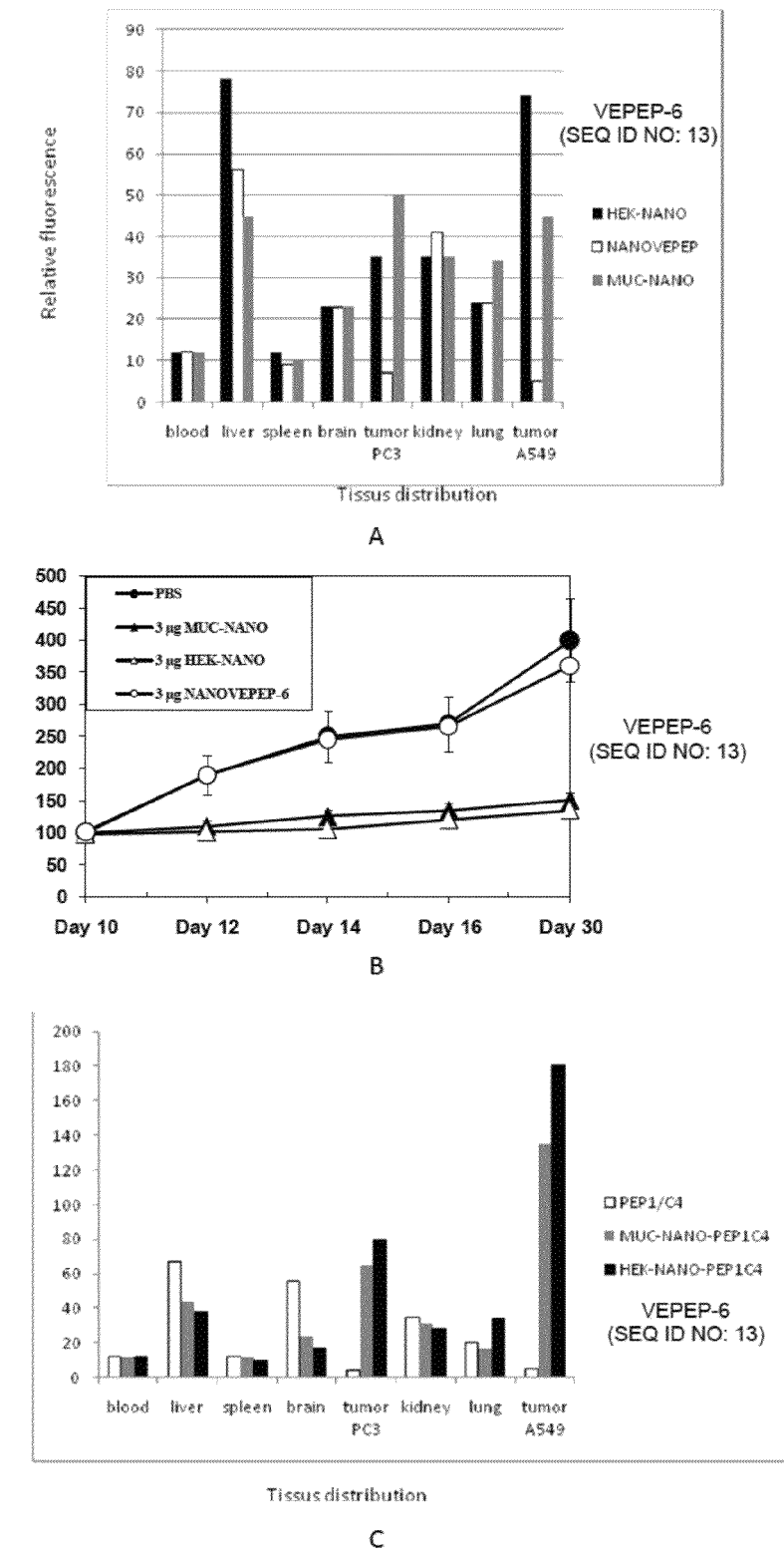

FIG. 12: NANOPEPHIS mediated Cyclin B1 siRNA or PEP1/PC4 delivery upon systemic injection. Athymic female nude mice were subcutaneously inoculated into the flank with 1×10$^6$ PC3 or A549 tumor cells. Panel A: Two weeks after tumour implant, when tumour size reached about 100 mm$^3$, animals were treated by a single intravenous injection of NANOPEP-6/siRNA (in white), MUC-NANOPEP-6-HIS/siRNA (in grey) or (HEK-NANOPE-6-PHIS/siRNA (in black). In all the cases, 5 μg of Alexa$^{700}$ labelled siRNA were used. At 24 hr, mice were euthanized and different organs were removed for quantification of Alexa fluorescence in the different tissues and normalized to the protein level in the sample. Panel B: Two weeks after A549 tumour implant, when tumour size reached about 100 mm$^3$, animals were treated every 3 days, by intravenous injection of either NANOPEP-6/siRNA (open circle), MUC-NANOPEP-6-HIS/siRNA (open triangle), HEK-NANOPEP-6-HIS/siRNA (closed triangle) or saline buffer solution (closed circle). In all cases, siRNA are complexed with NANOPEP-6 or NANOPEPHIS at a 1/20 molar ratio. Tumour diameter was measured in two directions at regular intervals using a digital calliper and tumour volume was calculated as length×width× height×0.52. Curves show the mean value of tumour size in a cohort of six animals and neither animal death nor any sign of toxicity were observed. Panel C: Two weeks after tumour implant, when tumour size reached about 100 mm$^3$, animals were treated by a single intravenous injection of PEP1/PC4 (in white), MUC-NANOPEP-6-HIS/PEP1/PC4 (in grey) or HEK-NANOPEP-6-HIS/PEP1/PC4 (in black). In all the cases, 10 μg of CY5-labelled PC4 were used. At 24 hr, mice were euthanized and different organs were removed for quantification of CY5 fluorescence in the different tissues and normalized to the protein level in the sample.

Figure 13:
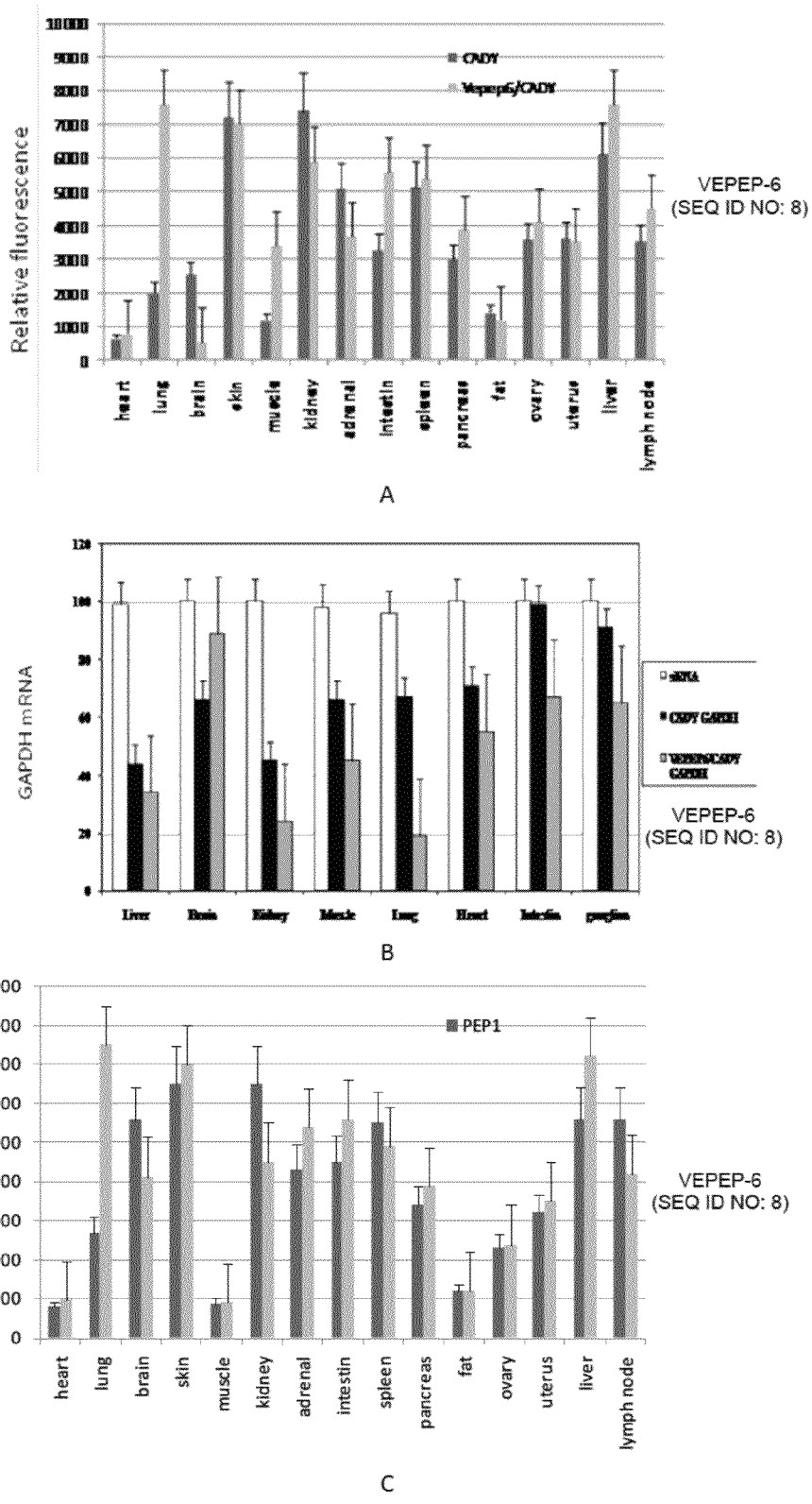

FIG. 13: NANOPEP-6-mediated in vivo targeted delivery in the lung. siRNA targeting GAPDH, Alexa$^{700}$ labelled or not, was complexed with CADY-peptide at ratio 1/20, then the CADY/siRNA "core shell" was coated by VEPEP-6 peptide at a 1/10 molar ratio (Panels A,B). A short 15-mer peptide labelled with CY5 dye was associated to PEP-1 peptide at a molar ratio 1/10, then PEP1/peptide "core shell" was coated by VEPEP-6 peptide at a 1/10 molar ratio (Pane C). In all the cases, 5 μg/of cargoes complexed with peptide carrier were injected intravenously. In vivo biodistribution of the core shell particles (in black) and of VEPEP-6 coated core shell particles (in grey) were monitored using live fluorescence animal imaging 48 hr after injection. Panel B: The biodistribution of CADY/siRNA complex coated or not with VEPEP-6 was also validated by monitoring the level of housekeeping gene mRNA GAPDH in the different tissues. A single injection of naked siRNA (in white: 100 μg), CADY/siRNA (in black: 5 μg) and NANOPEP-6/CADY/siRNA (in grey: 5 μg) was performed. The level of GAPDH mRNA was quantified in all the tissues using Quantigen technology. Reported data are the average of 3 separate experiments.

Figure 14:
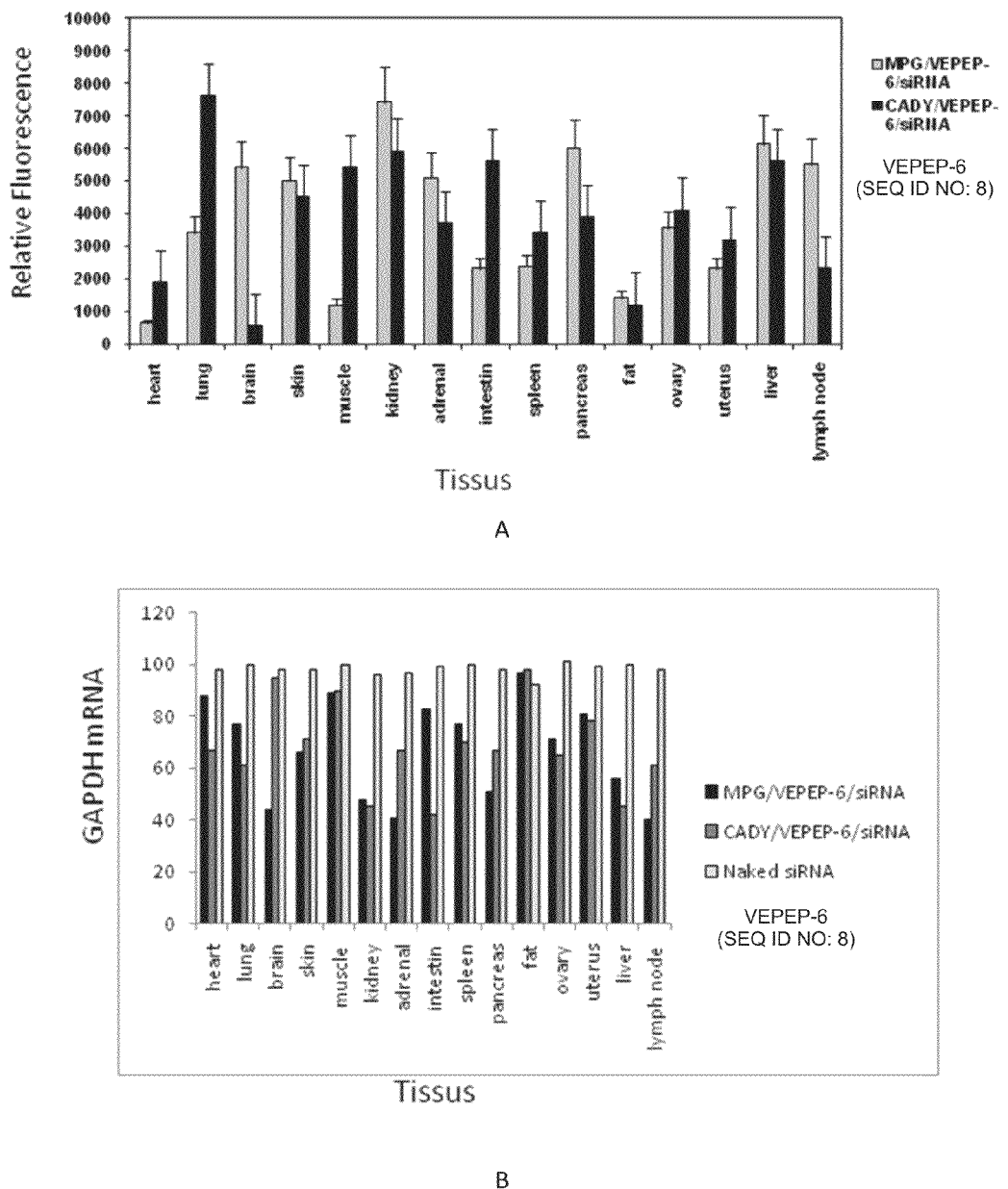

FIG. 14: CPP-mediated in vivo targeted delivery of VEPEP-6/siRNA complexes. siRNA targeting GAPDH, Alexa$^{700}$ labelled or not, was complexed with VEPEP-6-peptide at ratio 1/20, then the VEPEP6/siRNA "core shell" was coated by MPG or CADY peptide at a 1/10 molar ratio. In both cases, 5 μg of siRNA complexed with VEPEP-6 carrier were injected intravenously. Panel A: In vivo biodistribution of MPG/VEPEP6/siRNA (in black) and of CADY/VEPEP-6/siRNA particles (in grey) were monitored using live fluorescence animal imaging 48 hr after injection. Panel B: The biodistribution of VEPEP6/siRNA complex coated with MPG (In black) or CADY (in grey) was also validated by monitoring the level of housekeeping gene mRNA GAPDH in the different tissues. A single injection of naked siRNA (in white: 100 μg), MPG/VEPEP6/siRNA (in black: 5 μg) and MPG/VEPEP6/siRNA (in grey: 5 μg) was performed. The level of GAPDH mRNA was quantified in all the tissues using Quantigen technology. Reported data are the average of 3 separate experiments.

Figure 15:
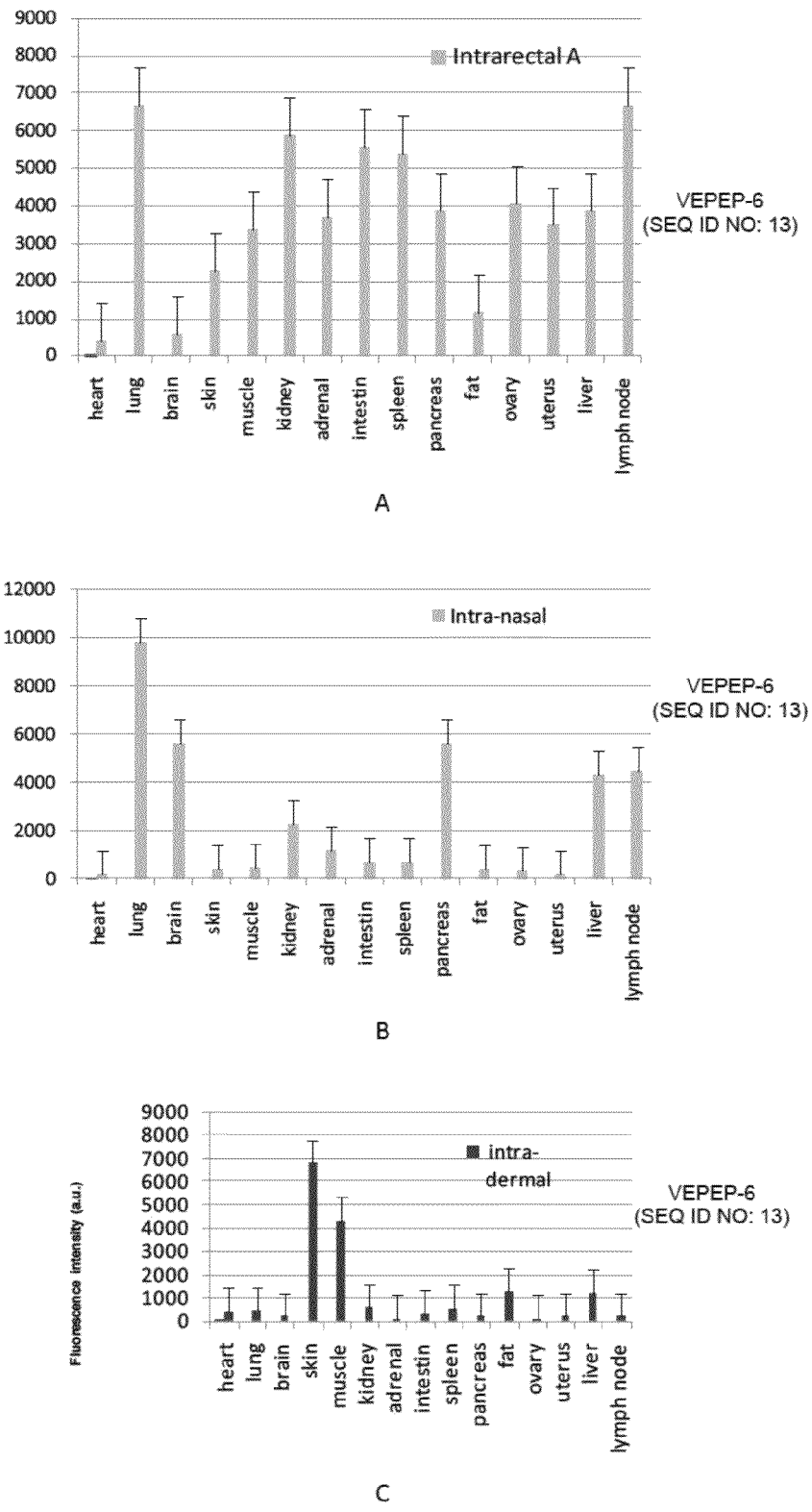

FIG. 15: NANOPEP-6 mediated siRNA delivery by dermal/intranasal and intrarectal administration. A fluorescently labelled siRNA with Alexa700 or a siRNA targeting the GAPDH was associated to VEPEP-6 as a "core shell" surrounded by VEPEP-6 molecules. Biodistribution of the fluorescently labelled siRNA was evaluated in vivo on Balb6 Mouse, 5 hr after a single intrarectal (Panel A), intranasal (Panel B) or intradermal (Panel C) administration of 10 μg of either naked siRNA or siRNA in NANOPEP-6 particles. Panel D: The siRNA associated GAPDH knock out was evaluated after 48 hr on different tissues, by monitoring the level of GAPDH mRNA using Quantigen technology (Panomics inc). Intravenous (light grey), intrarectal (in white), intranasal (in black) or intradermal (in light grey) administration. Reported data are the average of 3 separate experiments.

Figure 16:
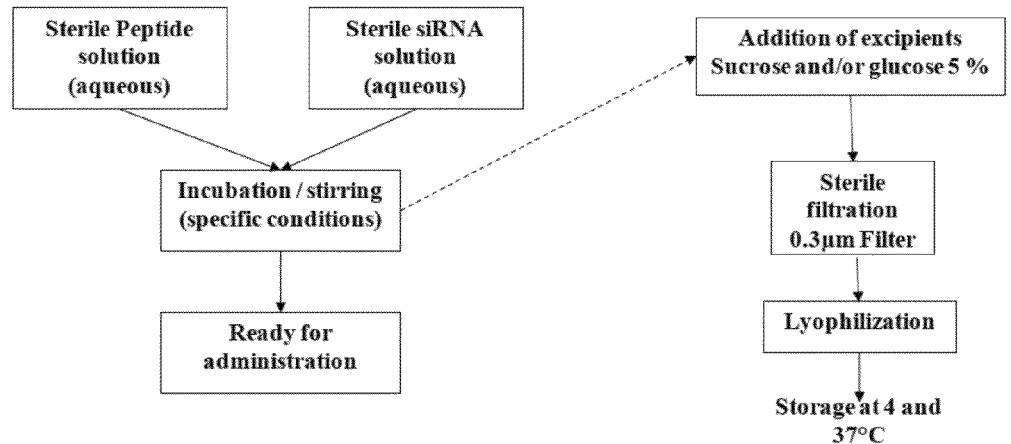

FIG. 16: Protocol for obtaining a fresh or a lyophilized formulation of VEPEP-6/siRNA complexes.

Figure 17:
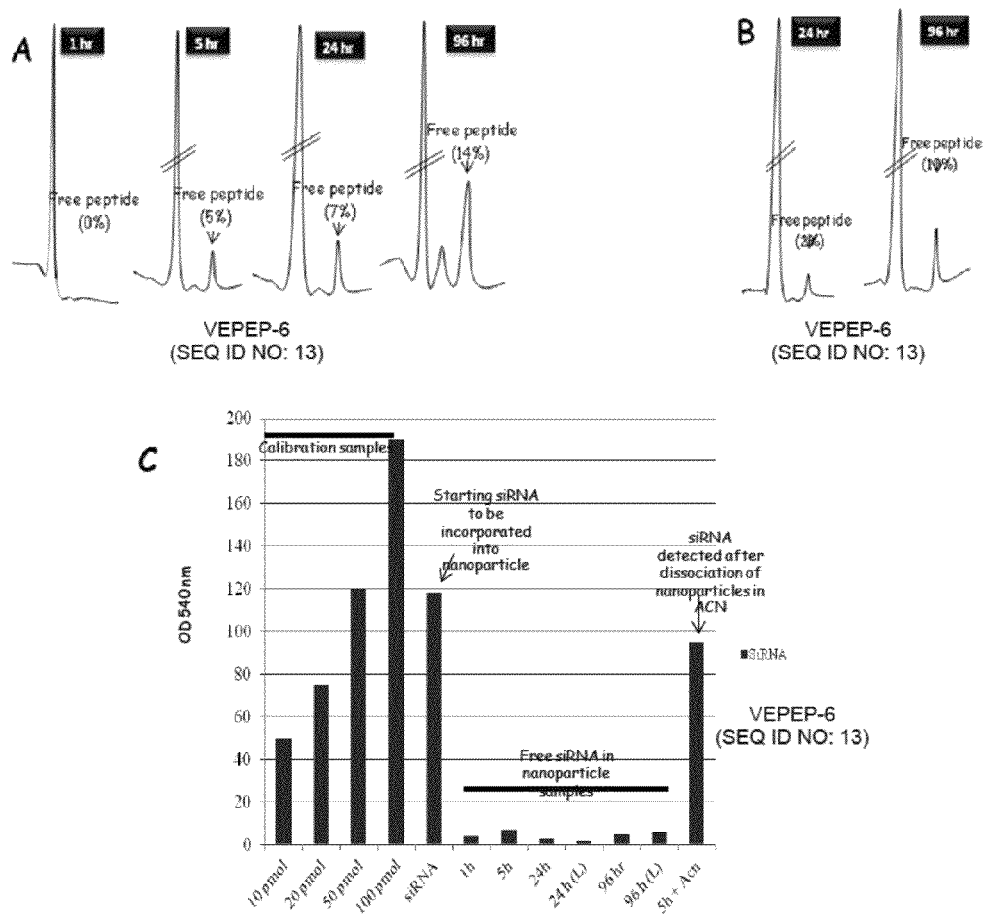

FIG. 17: VEPEP-6/siRNA samples were incubated at molar ratio 20:1 for 30 min at 25° C., then filtered using a 0.2 μm filter and analyzed by size exclusion HPLC chromatography using SEC 3000 after 1, 5, 24 and 96 hrs (panel A). Lyophilized VEPEP-6/siRNA in 5% glucose, were analyzed after 24 and 96 hr (panel B). Free siRNA was measured by quantigen technology (Affymetrix); quantification was based on calibration curve obtained with increasing doses of free siRNA. The level of siRNA within the particle was determined before particle formation and then after filtration of the particle using acetonitrile (ACN) for particle dissociation (Panel C).

Figure 18:
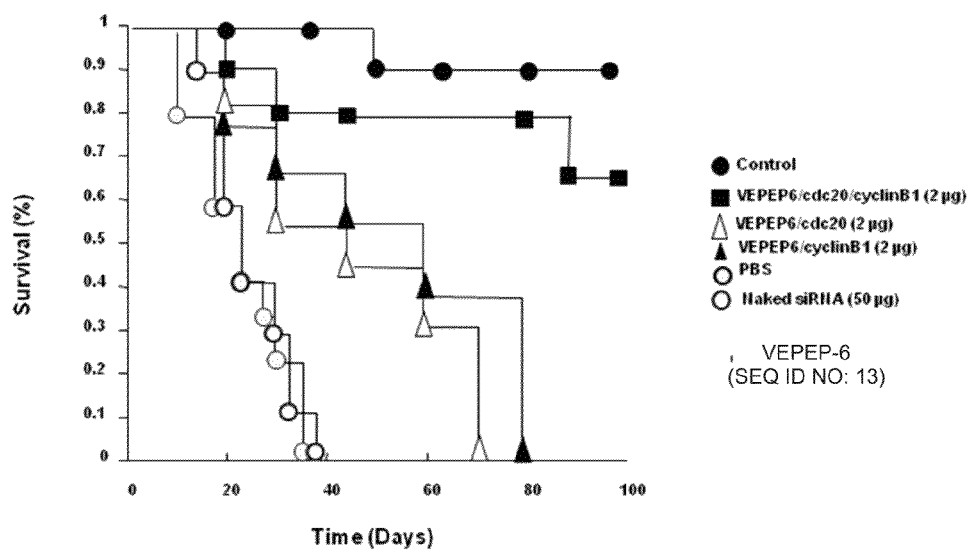

FIG. 18: NANOPEP-6 Cyclin B1/CDC20/GAPDH siRNA delivery upon systemic injection. Athymic female nude mice were subcutaneously inoculated into the flank with 1×10$^6$ PAN-1 (Pancreas-tumor). Five days after tumour implant, when tumour size reached about 100 mm$^3$, animals were treated by intravenous injections, every 4 days, with a solution either saline buffer solution (PBS, open circle), free siRNA cocktail (grey circle), Cyc-B1 siRNA (closed triangle) or CDC20 siRNA (open triangle) at 2 μg and siRNA cocktail at 2 μg (closed square) complexed with NANOPEP-6 at a 1/20 molar ratio. The curve with the closed circles corresponds to control animals without tumors. Curves show the mean value of survival in a cohort of ten animals and neither animal death nor any sign of toxicity were observed.

Figure 19:
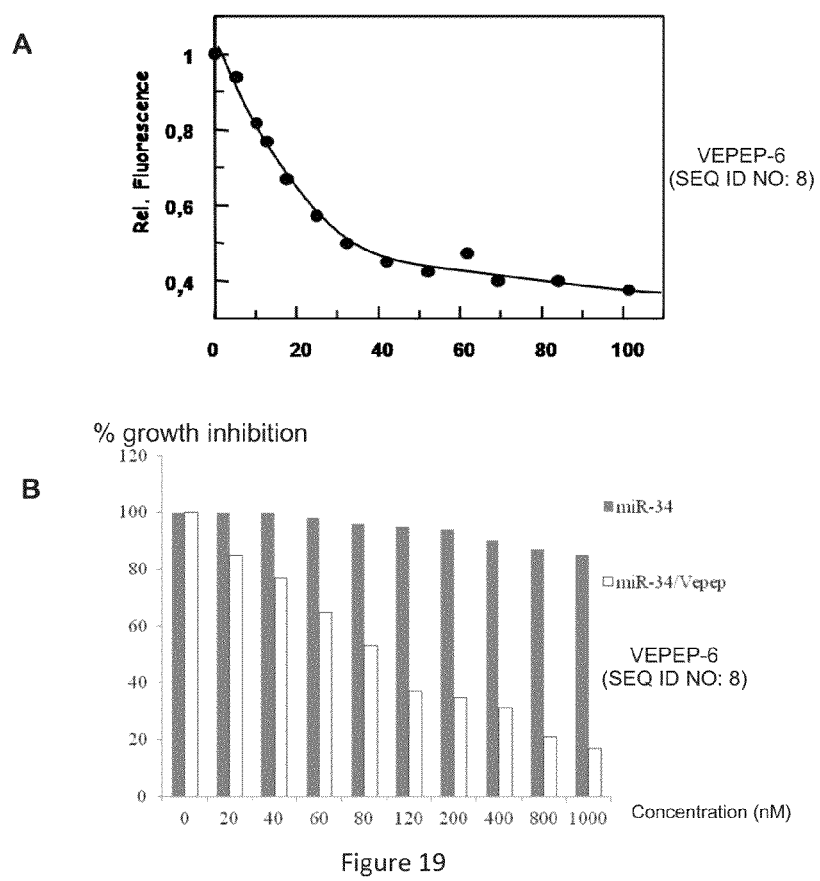

FIG. 19: VEPEP-6 Binding and delivery of miRNA (mir34 tumor supressor). Panel A: The binding of VEPEP-6 peptide for single stranded miRNA-34 was quantified by steady state fluorescence measurement using CY5-labelled mi34. A Fix concentrations of CY5-labelled mi34 (20 nM), was titrated by increasing concentrations of VEPEP-6 up to 100 nM. The fluorescence of CY5miRNA-34 was monitored at 550 nm upon excitation at 505 nm. Upon binding to mRNA-34, Vepep-6 induced a marked quenching of fluorescence. Data were fitted using a quadratic equitation and curves show the mean value of three different experiments. Panel B: Antiproliferation property of VEPEP-6 mediated delivery of miR34 onto MCF7 breath cancer cells. A stock solution of VEPEP-6/miRNA-34 particles (2 nM) was at molar ratio of 20/1 and lower concentrations were obtained by serial dilution of the stock solution in PBS. Single stranded miRNA-34 was associated to VEPEP-6 as a "core" shell surrounded by VEPEP-6 molecules. MCF-7 cell (confluency of 40%) were overlaid with preformed complexes white bars) or naked miRNA34 (grey bars) and cell proliferation was quantified after 4 days.

Figure 20:
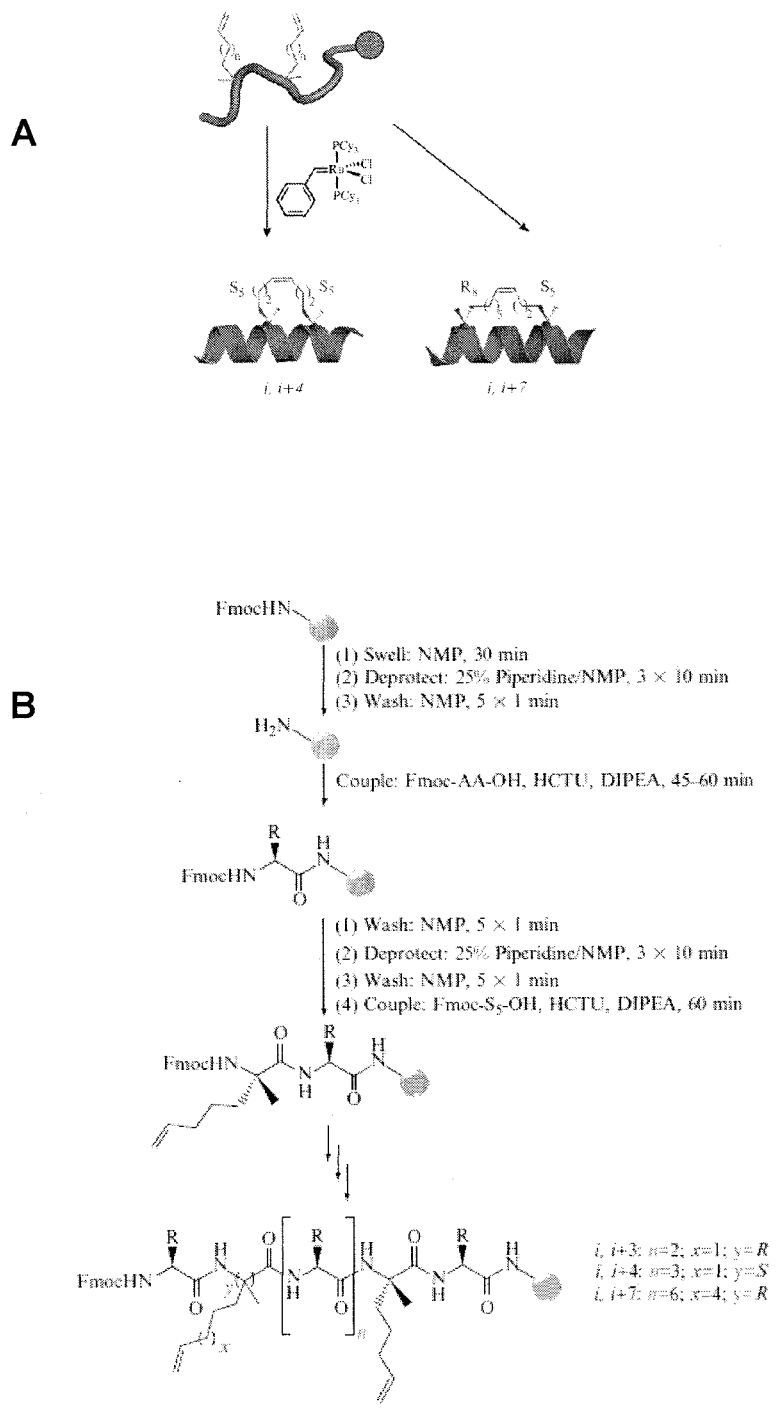

FIG. 20: Illustration of stapled VEPEP-6. (A) The two types of all-hydrocarbon stapled peptides. a-Methyl, a-alkenylglycine cross-linking amino acids are incorporated during solid-phase peptide synthesis. An i, i+4 stapled peptide requires two units of S5 (notations as in [18]) incorporated at the relative positions i and i+4 (ST-VEPEP-6a and ST-VEPEP-6b). An i, i+7 stapled peptide requires one unit of R8 at the i position and one unit of S5 at the i+7 position (ST-VEPEP-6C). Resin-bound peptide is treated with Grubbs I olefin metathesis catalyst to produce a cross-link between the two normatural amino acids, resulting in a stapled peptide that is braced in an α-helical conformation. (B) Fmoc-based solid-phase peptide synthesis of hydrocarbon stapled peptides (from Verdine & Hilinski, 2012).

Figure 21:
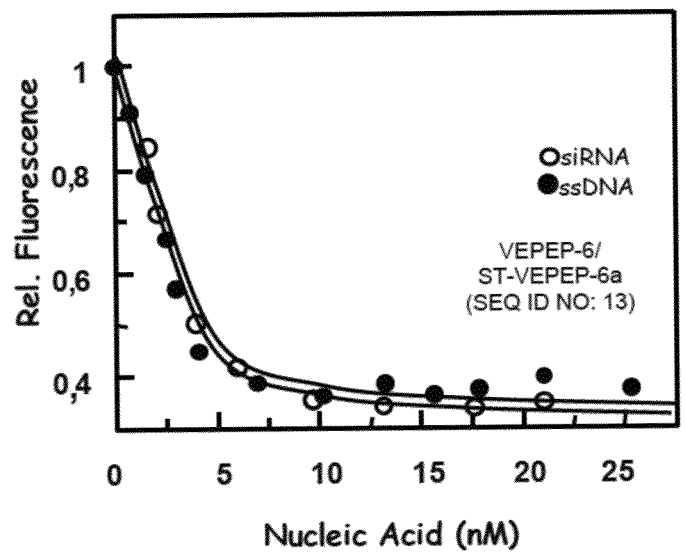

FIG. 21: Binding of small nucleic acids to stapled VEPEP-6 as monitored by fluorescence spectroscopy. Binding of nucleic acid to ST-VEPEP-6a was monitored by TRP-intrinsic fluorescence spectroscopy. Nucleic acids used: double stranded DNA (45/35 mer), siRNA (19/19 or 25/25) and single stranded DNA (19 or 36 mer). A fix concentration of ST-VEPEP-6a (50 nM) was titrated by increasing concentrations of nucleic acid, then dissociation constants were calculated from data fitting using a quadratic equation.

Figure 22:
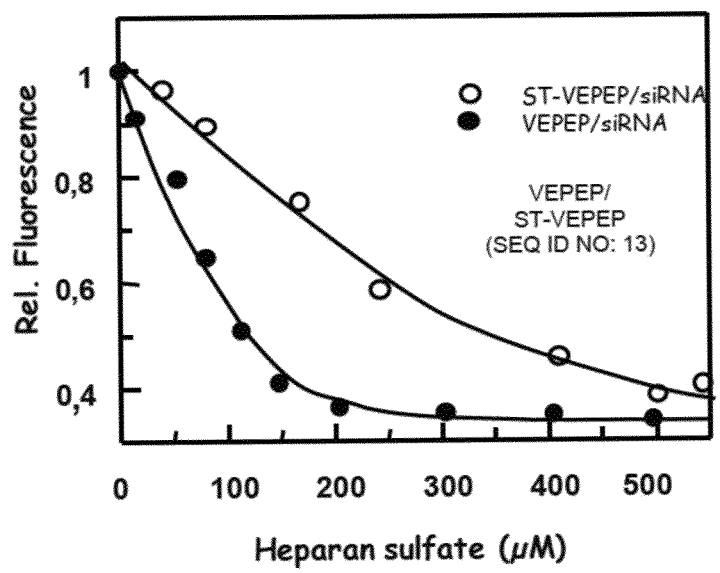

FIG. 22: Dissociation of siRNA/ST-VEPEP-6 and siRNA/VEPEP-6 complexes in the presence of heparan sulphate. Dissociation of siRNA/ST-VEPEP-6 and siRNA/VEPEP-6 complexes formed at 100 nM at a molar ratio of 20/1 was monitored by fluorescence spectroscopy, using FITC-labelled siRNA associated to ST-VEPEP-6a or VEPEP-6a. Preformed complexes were incubated with increasing concentrations of Heparan sulphate and dissociation was measured at 520 nM upon excitation at 492 nm. Dissociation constants were calculated from data fitting.

Figure 23:
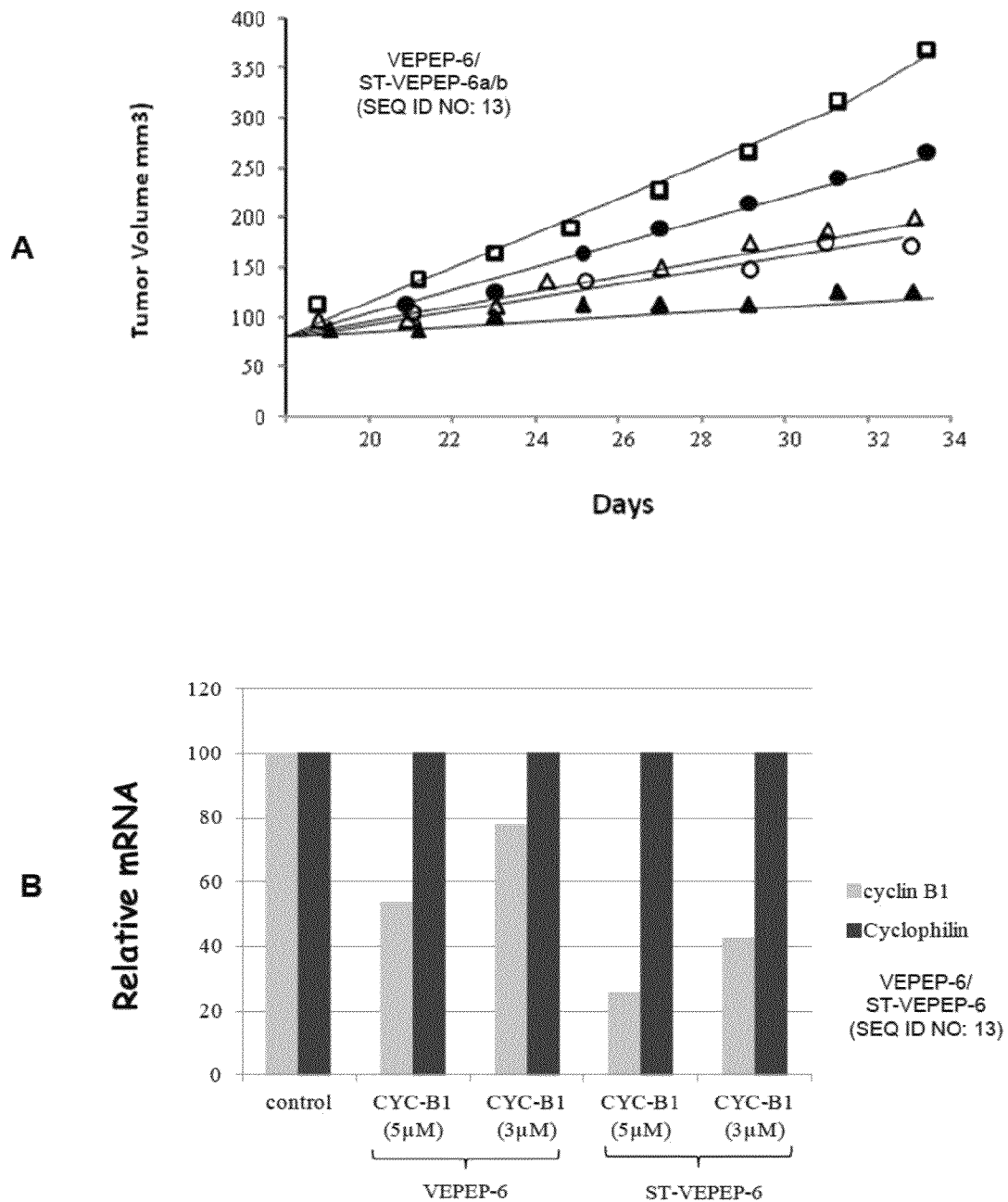

FIG. 23: ST-VEPEP-6 Cyclin B1 siRNA delivery upon systemic injection. Athymic female nude mice were subcutaneously inoculated into the flank with 1×10$^6$ HT29. When tumour size reached about 100 mm$^3$, animals were treated by intravenous injections, every 4 days, with a solution either saline buffer solution, free Cyc-B1 siRNA (open square), or Cyc-B1 siRNA at 3 μg (open symbol) or 5 μg (close symbol) complexed with VEPEP-6 (circle) or ST-VEPEP-6a or ST-VEPEP-6b (triangle) at a 1/20 molar ratio. Tumour diameter was measured in two directions at regular intervals using a digital calliper and tumour volume was calculated as length×width×height×0.52. Curves show the mean value of tumour size in a cohort of three animals and neither animal death nor any sign of toxicity were observed. (A) Increase of tumor volume upon treatment. (B) Target cyclin B1 mRNA level. After 48 days, HT29 tumors were removed, and Cyclin B1 mRNA levels were evaluated by Quantigen technology and normalized to cyclophilin levels. Control (black), 5 μg siRNA-cyc-B1 (grey) complexed with VEPEP-6 or ST-VEPEP-6a at a 1/20 molar ratio.

EXAMPLES

Example 1

Materials, Methods, Chemistry, and Biophysic Analysis

VEPEP-6 Peptides
All peptides were synthesized by solid-phase peptide synthesis using AEDI-expensin resin with (fluorenylmethoxy)- carbonyl (Fmoc) on a Pioneer Peptide Synthesizer (Pioneer™, Applied Biosystems, Foster City, Calif.) starting from Fmoc-PAL-PEG-PS resin at a 0.2 mmol scale. The coupling reactions were performed with 0.5 M of HATU in the presence of 1 M of DIEA. Protecting group removal and final cleavage from the resin were carried out with TFA/Phenol/H$_2$O/Thioanisol/Ethanedithiol (82.5/5/5/5/2.5%) for 3 h 30 min. All the peptides presented a cysteamide group at the C-terminus and were acetylated at the N-terminus. The peptide synthesis started by the C-terminus, using an AEDI-expensin resin starting with a cysteamide link, as described by Mery et al, 1992 [10]. All the peptides contained a beta-Alanine or a serine at the N-terminus to favour any further functionalization without using the C-terminal cysteamide group.

The following peptides were synthesized:

```
                                              (SEQ ID No: 7)
VEPEP-6a:
Ac-[βA/S]LFRALWRLLR[S/T]LWRLLW[K/R]-cysteamide (SEQ ID No: 8)
VEPEP-6b:
Ac-[βA/S]LWRALWRLWR[S/T]LWRLLW[K/R]A-cysteamide (SEQ ID No: 9)
VEPEP-6c:
Ac-[βA/S]LWRALWRL[L/C/I]R[S/T]LWRLWR[K/R]A-
cysteamide (SEQ ID No: 10)
VEPEP-6d:
Ac-[βA/S]LWRALWRLWR[S/T]LWRLWR[K/R]A-cysteamide (SEQ ID No: 11)
VEPEP-6e:
Ac-[βA/S]LWRALWRL[L/I]RALWRLLW[K/R]A-cysteamide (SEQ ID No: 12)
VEPEP-6f:
Ac-[βA/S]LWRALWRL[L/C/I]RNLWRLLW[K/R]A-cysteamide,
``` wherein the notation [X/Y] means that both amino acids X and Y have been tested at this position, with identical results.

Functionalization of Vepep-6

Two Approaches were Used for Peptide Functionalization (1) Peptide conjugations with peptide, antibody, pegylation, NTA, cholesterol, or stearylation were performed at the primary amino group of the N-terminal residue, through a beta alanine or serine. It is advantageous to maintain the C-terminal cysteamide free, since it is known to be required to stabilize the particle through disulfide bounds (SH—SH). Functionalized peptides were further purified by Reverse Phase-HPLC and analyzed by electro-spray ionization mass spectroscopy.

(2) Peptide conjugations were also performed via disulfide bound using the SH-group of the cysteamide moiety of the peptide.

```
                                       (SEQ ID No: 15) (1)
    VEPEP-6-Funct-1:
    X-ALFRALWRLLRSLWRLLWK-NH-CH₂-CH₂-SH (SEQ ID No: 16) (2)
    VEPEP-6-Funct-2:
    Ac-ALFRALWRLLRSLWRLLWK-NH-CH₂-CH₂-S-S-X
```

X: Cholesterol, Pegylation, stearyl, palmitoyl, small FC or FAB fragments, nitrilotriacetic acid (2×NTA) or targeting peptide (for example, brain targeting peptide).

Oligonucleotides & siRNA siRNAs and 5' Alexa$^{700}$ or fluorescein (5'-FAM) fluorescently labelled siRNA were synthesized by Eurogentec (Belgium) according to the following sequences.

```
                                             (SEQ ID No: 17)
Cyc-B1 sense
5'GGCGAAGAUCAACAUGGCATT3', (SEQ ID No: 18)
Cyc-B1 antisense
5'UGCCAUGUUGAUCUUCGCCTT3', (SEQ ID No: 19)
Cyc-B3 sense
5'GGUGAAGAUCAGCAUGGCATT3', (SEQ ID No: 20)
Cyc-B3 antisense
5'UGCCAUGUCGAUCUUCACCTT3', (SEQ ID No: 21)
GAPDH sense
5'CAUCAUCCCUGCCUCUACUTT-3',
and (SEQ ID No: 22)
GAPDH antisense
5'AGUAGAGGCAGGGAUGAUG3'.
```

Cyc-B1 siRNA targeting cyclin B1, and a derived siRNA harbouring two mismatches, Cyc-B3, was used as control. An siRNA targeting GAPDH was used as control to validate target specificity and to monitor associated non specific interferon response. The stock solution of siRNA was prepared in RNase free water.

VEPEP-6 Structure

VEPEP-6 peptides are secondary amphipatic peptides, they are highly versatile and show a strong structural polymorphism. VEPEP-6 are unfolded in solution as a free form and adopted an alpha helical conformation in the presence of lipid or artificial cellular membranes as well as in the presence of cargos such as siRNA/single stranded and double stranded oligonucleotides (FIG. 1).

Characterization of Peptide-Based Nanoparticles

Mean particle size distribution was determined with a Coulter N4 Plus (Coulter-Beckman) at 25° C. for 3 min per measurement and zeta potential was measured with Zetasizer 4 apparatus (Malvern Ltd,)

Cytotoxicity

Toxicity of VEPEP-6/siRNA complexes was investigated on Hela and HS-68 cell lines. 30,000 cells seeded in 24-well plated the day prior transfection, were incubated with increasing concentrations of siRNA complexed with VEPEP-6 at a 20/1 molar ratio ranging from 0.1 to 5 μM (100 μM VEPEP-6), for 30 min prior to addition of medium to reach a final 10% concentration of FCS. Cytotoxic response was measured 12 hr or 24 hr later by monitoring the housekeeping gene cyclophilin mRNA level (Quantigen, Panomic Inc.) and by colorimetric MTT assay (Sigma, Germany), respectively. For MTT assay, cell culture medium was removed and replaced with PBS containing 2.5 mg/ml of MTT for 4 hr. Results correspond to the average of 3 separate experiments.

In Vivo Imaging of siRNA Biodistribution

In vivo fluorescence imaging was performed as previously described [26, 27]. Mice were injected intravenously with 10 μg (200 μl) of Alexa700 fluorescently labelled siRNA either naked or complexed with different VEPEP-6-based formulations: example 5.2.1 NANOPEP-6-HIS/siRNA; example 5.3 NANOPEP-6/CADY/siRNA and NANOPEP-6/PEP1/peptide; Example 5.4 CADY/VEPEP6/siRNA and MPG/VEPEP6/siRNA, Example 5.5 NANOPEP-6/siRNA (n=3 animals per group). Anaesthetized mice, using 2% Isoflurane, were illuminated by 663 nm light emitting diodes equipped with interference filters and movies were acquired over the first 15 minutes and fluorescence images were taken every hour for 5 hrs and then after 24 hrs, with a back-thinned CCD cooled camera as previously described [11]. At 24 hr mice were euthanized and different organs were removed for quantification of Alexa fluorescence.

Example 2

VEPEP-6 Peptides Applications for Molecules Delivery

Example 2.1

VEPEP-6 Peptides Form Stable Nanostructures with Nucleic Acids

VEPEP-6 peptide form stable complexes with siRNA, single stranded and double stranded oligonucleotides. The binding of cargos to VEPEP-6 was monitored by fluorescence spectroscopy using the both intrinsic Trp group of VEPEP-6 (3 to 5 Trp-residues) and extrinsic fluorescently labeled cargoes (using Cy3, Cy5 or FITC). Fluorescence experiments were performed on a PTI spectrofluorimeter at 25° C. in a NaCl-154 mM buffer. Intrinsic Trp-fluorescence of VEPEP-6 was excited at 290 nm and emission spectrum was recorded between 310 and 400 nm, with a spectral band-pass of 2 and 8 nm for excitation and emission, respectively. FITC-fluorescence of labelled-siRNA or DNA was excited at 492 nm and emission recorded between 500 and 580 nm. For VEPEP-6/siRNA interaction, 0.5 µM of FITC-labelled siRNA was titrated by increasing concentrations of peptide. All measurements were corrected for the dilution and curve fitting were performed by using Grafit software (Erithacus). Curve fitting reveal that VEPEP-6 strongly binds the different cargoes with dissociation constant in the nanomolar range (Table 1 and FIG. 2).

Example 2.2

VEPEP-6 Peptides Form Stable Nanostructures with Small Hydrophobic Molecules VEPEP-6 peptides also form stable particles with small aromatic and/or hydrophobic molecules including daunomycin, Paclitaxel, doxorubicin, AZT, porphyrin, FAM-G or fluorescent dyes (FIG. 3). The dissociation constant for small hydrophobic molecule ranges between 0.03 to 4 µM, depending on the nature of the dyes and of the peptides.

TABLE 1

VEPEP-6/Cargo complexes characterization.

| | Cargoes | | | | | |
|---|---|---|---|---|---|---|
| | siRNA | | SS-DNA | | DD-DNA | |
| VEPEP-6 | Binding | Kd (nM) | Binding | Kd (nM) | Binding | Kd (nM) |
| VEPEP-6a: | yes | 10-20 | yes | 50-100 | yes | 200 |
| VEPEP-6b | yes | 10-20 | yes | 50-100 | yes | 200 |
| VEPEP-6c: | yes | 10-20 | yes | 50-100 | yes | 200 |
| VEPEP-6d: | yes | 10-20 | yes | 50-100 | yes | 200 |
| VEPEP-6e | yes | 10-20 | yes | 50-100 | yes | 200 |
| VEPEP-6f: | yes | 10-20 | yes | 50-100 | yes | 200 |

SS-DNA: single-stranded DNA; DD-DNA: double-stranded DNA.

TABLE 2

VEPEP-6/Cargo complexes characterization.

| | Cargoes | | | | | | | |
|---|---|---|---|---|---|---|---|---|
| | Doxorubicin | | porphyrin | | AZT | | FAM-guanosine | |
| VEPEP-6 | Binding | Kd (µM) | Binding | Kd (µM) | Binding | Kd (µM) | Binding | Kd (µM) |
| VEPEP-6a: | yes | 1 | yes | 4 | no | — | no | — |
| VEPEP-6b | yes | 0.7 | yes | 5 | no | — | no | — |
| VEPEP-6c: | yes | 0.03 | yes | 1.2 | yes | 0.3 | yes | 4 |
| VEPEP-6d: | yes | 0.5 | yes | 0.5 | yes | 0.1 | yes | 0.8 |
| VEPEP-6e | yes | 0.5 | yes | 0.2 | yes | 0.9 | yes | 2.3 |
| VEPEP-6f: | yes | 0.2 | yes | 0.2 | yes | 2.4 | yes | 2.8 |

SHM: small hydrophobic molecules (porphyrin, FAM-G, AZT, doxorubicin)

Similar results were obtained for Doxorubicin, paclitaxel and daunomycin.

Example 2.3

VEPEP-6 Peptides Form Stable Nanoparticles with their Different Cargoes

The size of the particles was monitored by dynamic light scattering. The optimal VEPEP-6 peptide/cargo molar ratio is ranging between 1/10 to 1/30 (FIG. 4). The size of the particles is of about 100 to 200 nanometers in diameter.

The complex formation was also analyzed by dynamic light scattering, electron scan microscopy (FIG. 5a) and atomic force microscopy (AFM) (FIG. 5b). Size of the particles was of 100 to 300 nm when measured with these technologies.

Example 3

VEPEP-6 Applications in Cultured Cells

Example 3.1

VEPEP-6 Mediated Delivery of siRNA in Different Cell Lines

VEPEP-6 peptides have been applied for the delivery of different siRNA into different cell lines, including adherent, suspension and challenging cell lines such as primary (Jurkat, CEM-ss, HUVEC, THP1 . . . ) and stem cell lines (mES, CCM . . . ). Cell lines (from American Type Culture Collection (ATCC)) were cultured in Dulbecco's Modified Eagle's Medium supplemented with 2 mM glutamine, 1% antibiotics (streptomycin 10'000 g/ml, penicillin, 10,000 IU/ml) and 10% (w/v) foetal calf serum (FCS), at 37° C. in a humidified atmosphere containing 5% $CO_2$. Stock solutions of VEPEP-6/siRNA particles were prepared by complexing 100 nM siRNA with VEPEP-6 peptides at a molar ratio of 1/20 for 30 min at 37° C. Lower concentrations of VEPEP-6-carrier/siRNA (from 20 nM to 0.125 nM) were obtained by serial dilution of the stock complexes in PBS, in order to preserve the same VEPEP-6-carrier/siRNA ratio. 150 000 cells seeded in a 35 mm dish the day prior transfection, were grown to 60% confluence and overlaid with 2001 of preformed complexes, incubated for 3-5 min, then 4001 of DMEM were added. After 30 min. incubation at 37° C., 1 ml of fresh DMEM containing 16% foetal calf serum (FCS) was added in order to reach a final FCS concentration of 10%, without removing the overlay of VEPEP-6/siRNA complexes. Cells were returned to the incubator for 24 hrs. Dose-response experiments performed on different cultured cells revealed that VEPEP-6-mediated delivery of siRNA (GAPDH) induced a robust downregulation of both GAPDH protein and mRNA levels (Table 3). In most of the cell lines, knock out (KO) higher than 70% was obtained at the protein level. Table 4 provides another series of cell lines on which VEPEP-6 have been shown to induce more that 60% KO of GAPDH.

TABLE 3

| Cell lines | origin | efficacy |
|---|---|---|
| Hela | Human epithelial cervical cancer cells | 75% |
| Jurkat | Human T lymphocyte | 70% |
| HepG2 | Human hepatocyte | 80% |
| C2C12 | Mouse myoblast | 80% |
| MEF | Mouse fibroblast | 90% |
| HS-68 | Human fibroblast | 90% |
| CEM-SS | Human macrophage | 80% |
| U2OS | Human osteoblast | 91% |
| MCF7 | Human breast adenocarcinoma | 68% |
| MT4 | Human T lymphocyte | 70% |
| HER2 | Human breast cancer | 90% |
| MDA-MB | Human breast cancer | 85% |

TABLE 4

| Cells | origin |
|---|---|
| Balb/c3T3 | differentiated mouse adipocytes |
| C2C12 | differentiated mouse myotubes |
| C2C12 | undifferentiated mouse myocytes |
| RAW 264.7 | mouse macrophage cells |
| U87MG | Human brain glioblastoma astrocytoma cells |
| Astrocytoma cells | Human |
| NHEK-AD | primary human adult keratinocytes |
| THP-1 | Human peripheral blood acute monocytic leukemia cells |
| HUVEC | Human umbilical vein endothelial cells |
| HT29 | Human colon carcinoma cells |
| SWG20 | Human colon carcinoma cells |
| BSMC | Human bronchial smooth muscle cells |
| A549 | Human lung carcinoma cells |
| A2780 | Human ovarian cancer cells |
| ASPC-1 | Human pancreatic carcinoma |
| mES | Mouse embryonic stem cells |
| CCM | Primary chicken cardiac embryonic myocyte |
| MPN | Primary mouse neuronal cells |

Example 3.2

VEPEP6-Mediated Delivery of siRNA Targeting Cyclin B1 Induces G2 Arrest

Dose-response experiments performed on cultured cells revealed that VEPEP-6-mediated delivery of siRNA (Cyc-B1) induced a robust biological response associated with downregulation of both cyclin B1 protein and mRNA levels (FIG. 6). Cyclin B1 mRNA and protein levels were determined 12 and 24 hrs following transduction, using Quantigen (Panomics Inc.) and Western blotting, respectively. Mouse monoclonal anti-Cyclin B1 antibodies (SC-245) and rabbit polyclonal anti-Cdk2 antibodies (SC-163) were obtained from Santa Cruz Biotechnology Inc. Data reported are an average of 3 or 4 distinct experiments. A siRNA concentration of 5 nM was sufficient to reduce cyclin B1 levels by more than 85% in Hela cells and $IC_{50}$ of 1.7±0.7 nM and 1.9±0.3 nM were estimated for downregulation of protein levels, and of 0.7±0.1 nM and 0.5±0.1 nM for mRNA levels, for non-transformed HS68 fibroblasts (FIG. 6) and HeLa cells, respectively.

Reduction of cyclin B1 protein levels was directly associated with accumulation of cells with a 4N content, consistent with downregulation of Cdk1-Cyclin B1 activity, and was optimally obtained with 2 nM siRNA and $IC_{50}$ values estimated to 1.2±0.2 nM and 1.7±0.4 nM for HeLa and HS68 cells, respectively (FIG. 6C). In contrast, no effect on cyclin B1 levels and cell cycle progression was observed with 200 nM of an unrelated siRNA (si-GAPDH), or of a mismatch siRNA harbouring two mutations (Cyc-B3) complexed with VEPEP-6 at a 1/20 ratio, or with VEPEP-6 carrier alone (100 µM).

Example 3.3

VEPEP6-Mediated Delivery of siRNA is not Toxic

As shown on FIG. 7A, the toxicity of VEPEP-6 particles was investigated on HeLa cells by MTT assay and by monitoring the level of cyclophilin mRNA measured by Quantigen™ technology (Affymetrix). No toxicity was detected at levels up to 10 nM, and only a mild toxicity was observed at the maximum concentration of 100 nM. VEPEP-6 and NANOPEP-6 (VEPEP6/VEPEP6/siRNA) did not induce immune response in vivo. As toxicity has been one of the major causes of failure of siRNA delivery systems, the impact of the VEPEP-6 and NANOPEP-6 particles on non specific cytokine induction has been investigated 6 h and 24 h after IV injection. Cytokine induction was monitored using the multiplex 10 cytokine KIT from invitrogen. As shown on FIG. 7B, no induction of cytokine was observed after 6 h and 24 h, in contrast to control lipid-based formulation or Lipopolysaccharide (LPS).

Example 3.4

VEPEP-6 Mediated Delivery of Small Hydrophobic Molecule in Different Cell Lines

VEPEP-6 peptides have been applied for the delivery of different small fluorescent hydrophobic molecules and doxorubicin on different cell lines including primary cell lines and challenging cell lines. VEPEP-6 peptides also form stable particles with small aromatic molecules including doxorubicin or fluorescent dyes (FIG. 8 and FIG. 9). The dissociation constant for small hydrophobic molecules ranges between 0.1 to 4 µM, depending on the nature of the dyes and of the peptides.

Example 4

NANOPEP-6 Formulations and Applications for In Vivo Delivery

NANOPEP-6 particles contain a "peptide-core" or "core shell" corresponding to the association of either VEPEP-6 peptide or any other peptide forming non covalent complexes with its respective cargo, that is surrounded by additional VEPEP-6 "peripheral" peptides stabilizing the particle and favouring cell membrane association. The efficacy of NANOPEP-6 is mainly controlled by the size and the charge of the particles, which should be ranging between 100-200 nm and +10-+20 Volts, respectively. Several combinations can be used for the "core" and peripheral VEPEP-6 can be functionalized or not. The choice of the peptides in the "core" is dependent on the nature of the cargoes and can be, for example, VEPEP-6, CADY [12], MPG [11] or PEP-1 [8].

The NANOPEP-6 particles are formed in a two step process (FIG. 10A): first the "core" at molar carrier/cargo ratio of 5/1 or 10/1, then the "peripheral" at a peripheral VEVEP-6/cargo molar ratio of 20/1 up to 80/1. The multilayer organization of the particle allows their oriented functionalization, that will be chosen depending on the nature of the cellular target/tissue and administration mode.

A three step protocol (FIG. 10B) has been established when particle functionalization takes place via the nitrilotriacetic acid (NTA) linked to the VEPEP-6. NTA-group is well known as being able to chelate metal and to strongly interact with histidine tagged protein. Coating of the particles with NTA-functionalized VEPEP-6 allows the attachment any protein harboring a histidine tag to the particle. That strategy offers the major advantage of having a common 2 layers particles "NANOPEP-6-HIS" that can be associated to any His-tagged protein. The NANOPEP-6-HIS strategy has been applied to coat the particles with specific antibody targeting cell surface antigen (EGF, HER-2 or MUC1) for targeted-delivery of siRNA and peptide (see example 5.2.1 for siRNA delivery and example 5.2.2 for peptide delivery using MUC1 and HER2-antibodies). NANOPEPHIS-6 strategy can be universally applied to any peptides and proteins harboring a Histidine cluster in their sequence.

Example 5

NANOPEP-6 Strategy Applications

NANOPEP-6 strategy has been applied for in vivo delivery and targeting of different cargos and different peptide-based nanoparticles. Four different examples of NANOPEP-6 and NANOPEPHIS-6 applications are reported thereafter.

Example 5.1

NANOPEP-6 Mediated siRNA In Vivo Targeted Delivery after Systemic Intravenous Injection or Topical Injection The therapeutic potential of the NANOPEP-6 technology has been evaluated in vivo with siRNA targeting either GAPDH and cyclin B1, a non-redundant mitotic cyclin. The potency of this technology has been validated in vivo with siRNA targeting cyclin B1, a non-redundant mitotic cyclin and established therapeutic target in several cancers, which forms together with Cdk1 kinase, the "Mitosis Promoting Factor" required for entry and progression through mitosis.

Athymic female nude mice (6-8 weeks of age) were subcutaneously inoculated into the flank with $1 \times 10^6$ PC3 (prostate cancer), A549 (lung cancer) or SCK-3-HEK2 (ovarian cancer) cells in 100 µl PBS. Two to three weeks after tumour implant, when tumour size reached about 100 mm$^3$, animals were treated by intratumoral or intravenous injection, every 3 days, with a solution of 0.1 ml of either free Cyc-B1 siRNA (50 or 100 µg), control siRNA Cyc-B3 or Cyc-B1 siRNA (1, 5, 10 µg) complexed within NANOPEP-6 particles. The "core" shell of the particles was formed using VEPEP-6 peptide at a molar ratio of 10/1 or 20/1 with a siRNA targeting cycline B1. siRNA stock solutions are in 50 mM Tris, 0.5 mM EDTA buffer or in RNase free water. VEPEP-6 peptides were solubilised in water and stock solution of peptide was sonicated for 10 min in a water bath before complex formation. Then VEPEP-6/siRNA complexes were formed by adding siRNA into the peptide solution and incubating at 37° C. for 20-30 minutes to allow the carrier peptide/siRNA complexes to form. NANOPEP-6 particles contain a VEPEP-6/siRNA "core shell" surrounded by additional VEPEP-6 or Chol-VEPEP-6 at a 1/20 molar ratio. Formulations containing 15% Chol-VEPEP-6 were prepared in a stepwise fashion by first forming a precomplex of VEPEP-6/siRNA at molar ratio of 20/1, followed by addition of Chol-VEPEP-6 so as to increase the ratio of carrier/siRNA to 40/1.

Tumour diameter was measured in two directions at regular intervals using a digital calliper and tumour volume was calculated as length×width×height×0.52. Curves show the mean value of tumour size in a cohort of six animals and neither animal death nor any sign of toxicity were observed. Experiments were performed according to national regulations and approved by the local animal experimentation ethical committee. The statistical significance of the results was calculated by Student's t test and p<0.05 considered to be statistically significant. The stock solutions of particles are performed in water and stable for at least three weeks at 4° C. Particles can be lyophilized for long time storage; in that case, 5 to 20% of glucose is added to the particle solution before lyophylization to stabilize the particles during the process. Before administration the particles are diluted in physiological conditions, in the presence: 0.9% NaCl and 5 to 20% glucose.

The inventors demonstrated that combining cyclin B1 siRNA with NANOPEP-6 prevents lung, ovarian and prostate tumour growth in xenografted mouse models, upon injection every three days of NANOPEP-6/siRNA complexes (FIG. 11).

NANOPEP-6 Cyclin B1 siRNA Delivery Upon Topical Injection

The potential of NANOPEP-6 (VEPEP6/VEPEP6) to deliver cyclin B1 siRNA in vivo was first evaluated on human prostate carcinoma cell PC3-xenografted mice (FIG. 11A). The effect of local intratumoral administration of NANOPEP-6/siRNA particles (molar ratio 20/1) on the growth of established subcutaneous tumours was evaluated. At day 50, tumor sizes in the control cohort, injected with PBS increased by about 3.5 fold. Reduction of tumor growth by 75% was observed using 1 µg (0.05 mg/kg) of cyclin B1 siRNA in NANOPEP-6/siRNA and tumour growth was completely prevented with 5 µg (0.25 mg/kg) of cyclin B1 siRNA in NANOPEP-6/siRNA (FIG. 11A). At day 48, it was validated that the Cyc-B1 siRNA mediated inhibition of tumour growth was directly associated with a decrease in the level of cyclin B1 mRNA. As a control, the inventors showed that administration of 100 µg (intratumoral or intravenous) naked siRNA or NANOPEP-6 carrier alone had no significant effect on tumour growth. Moreover, inhibition of tumour growth was siRNA sequence-specific as a cyclin B1 siRNA harbouring two mutations (Cyc-B3) complexed with NANOPEP-6 and injected into mice at 0.5 mg/kg was unable to inhibit tumour growth.

NANOPEP-6 Cyclin B1 siRNA Delivery Upon Systemic Injection

NANOPEP-6 particles were used for systemic intravenous administration into two xenografted tumor mouse models:

human prostate carcinoma (PC3) and ovarian cancer cells (HT29) injected subcutaneously into the flanks of NCR nude mice. NANOPEP-6/siRNA particles were obtained stepwise by complexing siRNA molecules with VEPEP-6 at a molar ratio of 10/1, followed by coating of particles with a second layer of VEPEP-6 at ratio 10/1. Five micrograms (0.25 mg/kg) and 10 µg (0.5 mg/kg) of Cyc B1 siRNA in NANOPEP-6 particles were injected intravenously every three days into mice bearing PC3 or HT29 xenografted tumors. A significant reduction in PC3 tumor size was observed at day 50, with 60% and 92% inhibition with 5 µg and 10 µg of siRNA, respectively (FIG. 11B). The reduction in tumour size was directly correlated to reduction of cyclin B1 protein levels, as evaluated by Western blotting, by 60% and 80% in animals treated with 5 µg and 10 µg of siRNA complexed to NANOPEP-6, respectively. A significant reduction in HT29 tumor size was observed at day 50, with 35% and 70% inhibition with 5 µg and 10 µg of siRNA, respectively (FIG. 11C). These results together with the lack of anti-tumoral activity of the NANOPEP-6/mismatch siRNA (10 µg) or of NANOPEP-6 carrier alone, underscores the robustness and specificity of the biological response associated with systemic delivery of cyclin B1 siRNA. The stability of drug-carrier formulations in vivo and in the blood circulation is a major issue for systemic administration of therapeutics. In order to improve the bioavailability and stability of the NANOPEP-6/siRNA (VEPEP-6 coating a VEPEP6/siRNA core shell) particles, thereby rendering them more suitable for systemic administration, the surface layer of NANOPEP-6 particles was functionalized with a cholesterol-moiety at the N-terminus of VEPEP-6 (Chol-VEPEP6), through activation of the N-terminal beta alanine amino group. Cholesterol-functionalized NANOPEP-6/siRNA particles were obtained stepwise by complexing VEPEP-6 molecules with siRNA at a molar ratio of 20/1, followed by coating of particles with a second layer of Chol-VEPEP6 at ratio 1/10. In order to analyze if increase in the distribution of siRNA associated to functionalized-NANOPEP-6 particles directly affects its potency to inhibit tumour growth, the particles were used for systemic intravenous administration into HT29 xenografted tumor mouse model. Two µg (0.25 mg/kg) of Cyc-B1 siRNA complexed with chol-NANOPEP-6 at a 1/30 ratio were injected intravenously every three days into mice bearing HT29 xenografted tumor and a significant reduction in HT29 tumor size of 85% was observed at day 50 (FIG. 11B), which is 5 fold more potent than the non functionalized-NANOPEP-6 nanoparticle, suggesting that cholesterol increases the biodistribution of siRNA in the tumour by maintaining siRNA in the plasma Example 5.2

NANOPEPHIS-Mediated In Vivo Targeted Delivery in Tumor after Systemic Intravenous Injection 5.2.1 NANOPEPHIS-Mediated In Vivo Targeted Delivery of siRNA in Tumor after Systemic Intravenous Injection The VEPEP-6/siRNA core shell particles were coated with NTA functionalized VEPEP-6 peptide and then incubated with his-tagged MUC1 or HEK-2 antibodies, known to target tumour cells. The excess of antibodies was removed by filtration before in vivo IV injection. The NANOPEP-6-HIS/siRNA particles were administrated by systemic IV injection into xenografted human prostate (PC3) and lung (A549) carcinoma mouse models. PC3 and A549 cells were injected subcutaneously into the flanks of NCR nude mice. 1 µg (0.05 mg/kg) and 5 µg (0.25 mg/kg) of Cyc-B1 siRNA complexed with MUC-NANOPEP-6-HIS/siRNA or HEK-NANOPEP-6-HIS/siRNA at a 40/1 molar ratio were injected intravenously every three days into mice bearing PC3 or A549 xenografted tumour. The level of siRNA release in the tumor was determined by live fluorescence imaging using An Alexa-700 fluorescently-labelled siRNA. Live fluorescence imaging experiments demonstrated that the presence of MUC or HER-2 antibodies significantly increased the level of siRNA in the tumour (5 to 10 folds depending on the antibody and the tumors (see FIG. 12 and table 5).

TABLE 5

NANOPEP-6 mediated delivery of fluorescently labelled siRNA in PC3 and A549 xenografted tumour in mice.

| Formulations | siRNA delivery in PC3 (fold increase) | siRNA delivery in A549 (fold increase) |
|---|---|---|
| NANOPEP-6 | 1 | 1 |
| MUC-NANOPEP-6-HIS | 5 | 12 |
| HEK-NANOPEP-6-HIS | 7 | 8 |

A significant reduction in PC3 or A549 tumor size was observed at day 30, with 55% and 95% inhibition with 1 µg and 5 µg of siRNA, respectively (FIG. 12b). The reduction in tumour size is at least 5-fold more efficient with the MUC-NANOPEPHIS/siRNA or HEK-NANOPEPHIS/siRNA, than with the NANOPEP-6/siRNA.

Example 5.2.2

NANOPEPHIS-Mediated In Vivo Targeted Delivery of Peptide in Tumor after Systemic Intravenous Injection The PEP1/peptide C4 (PC4: a 12 mer-peptide reported to block cancer cell proliferation: ref 13) core shell particles were coated with NTA functionalized VEPEP-6 peptide and then incubated with his-tagged MUC1 or HEK-2 antibodies. The excess of antibodies was removed by filtration before in vivo IV injection. The NANOPEP-6-HIS/PEP1/PC4 particles were administrated by systemic IV injection into xenografted human prostate (PC3) and lung (A549) carcinoma mouse models. PC3 and A549 cells were injected subcutaneously into the flanks of NCR nude mice. NTA-functionalized VEPEP-6 peptides were complexed with 10 µg of PEP1/PC4 particles at a 20/1 VEPEP-6/PC4 molar ratio and then with HIS-tagged antibodies to form MUC-NANOPEP-6-HIS/PEP1/PC4 or HEK-NANOPEP-6-HIS/PEP1/PC4 particles, which were injected intravenously into mice bearing PC3 or A549 xenografted tumour. The level of PC4 release in the tumour was determined by live fluorescence imaging using a CY5-labelled PC4. Live fluorescence imaging experiments demonstrated that the presence of MUC or HER-2 antibodies significantly increased the level of PC4 in the tumours (15 to 40 folds depending on the antibody and the tumours (see FIG. 12c and table 6).

TABLE 6

NANOPEP-6-mediated delivery of fluorescently labelled peptide in PC3 and A549 xenografted tumour in mice.

| Formulations | siRNA delivery in PC3 (fold increase) | siRNA delivery in A549 (fold increase) |
|---|---|---|
| PEP1/PC4 | 1 | 1 |
| MUC-NANOPEP-6-HIS/PEP1/PC4 | 15 | 35 |
| HEK-NANOPEP-6-HIS/PEP1/PC4 | 20 | 40 |

Example 5.3

NANOPEP-6-Mediated In Vivo Delivery of Peptide Based Nanoparticles for Therapeutic siRNA and Peptide and Lung Targeting VEPEP-6 peptides were used to promote lung targeting of peptide-based nanoparticles. VEPEP-6 peptide was added as a coating peptide on VEPEP-6/siRNA, CADY/siRNA and PEP-1/peptide "core shell particles" (FIGS. 13b and 13c). The cargos used were either a fluorescently-labelled siRNA or a peptide, or a siRNA targeting the housekeeping gene GAPDH. Particles were formed as reported in FIG. 10. In all the cases, 5 g of cargoes complexed with peptide carrier were injected intravenously. Then the in vivo biodistribution of the cargos was monitored using live fluorescence animal imaging and by monitoring the level of housekeeping gene mRNA 48 hr after injection. The presence of VEPEP-6 coating induced an important increase of the cargoes delivery in the lung (FIG. 13a and 13b). Monitoring fluorescence labelled cargoes showed a 5 to 10-fold increase in the lung, in comparison to control experiment in the absence of VEPEP-6 coating of the particle. The presence of VEPEP-6 coating also increased by a factor of 3 the knockdown of GAPDH in the lung (FIG. 13c). Taken together, these results demonstrated that VEPEP-6 peptide improves significantly lung targeting of peptide-based nanoparticles.

Example 5.4

CPP-Mediated In Vivo Targeted Delivery of VEPEP-6/siRNA Complexes

MPG and CADY cell penetrating peptides were used to promote different in vivo targeting of VEPEP-6/siRNA nanoparticles. The "core shell particles" VEPEP-6/siRNA were formed at 20/1 molar ratio and then MPG or CADY peptides were added as a coating peptide at a molar ratio 20/1, as reported in FIG. 10. In both cases, 5 µg of siRNA targeting the housekeeping gene GAPDH complexed with peptide carrier were injected intravenously. Then the in vivo biodistribution of the siRNA was monitored using live fluorescence animal imaging and by monitoring the level of housekeeping gene mRNA 48 hr after injection. Biodistribution of the fluorescently labelled siRNA was evaluated in vivo on Balb6 Mouse, 5 hr after a single administration of 5 µg siRNA in MPG/VEPEP-6 or CADY/VEPEP-6 particles. The presence of MPG or CADY coating induced an important increase of the siRNA delivery in most of the tissues. MPG specifically targets the brain, pancreas, lymph nodes and CADY the lung, muscle, heart and intestine (FIG. 14a). The presence of CADY or MPG coating also promotes a marked knockdown of GAPDH in the selected tissues (FIG. 14b). Taken together, these results demonstrated that VEPEP-6/siRNA core shell can be coated by several other CPPs to improve in vivo tissue targeting of peptide-based nanoparticles.

Example 5.5

NANOPEP-6 Mediated Topical Application of Peptide-Based Nanoparticles: Dermal/Intranasal and Intrarectal Administration NANOPEP-6 (VEPEP-6/VEPEP-6) based particles have been evaluated using different administration routes including systemic intravenous, intrarectal, intranasal and transdermal administration. A fluorescently labelled siRNA with Alexa700 or a siRNA targeting the GAPDH was associated to VEPEP-6 as a "core shell", surrounded by VEPEP-6 molecules. Biodistribution of the fluorescently labelled siRNA was evaluated in vivo on Balb6 Mouse, 5 hr after a single administration of 10 µg siRNA in NANOPEP-6 particles. The siRNA associated GAPDH knock out was evaluated after 48 hr on different tissues, by monitoring the level of GAPDH mRNA using Quantigen technology (Panomics inc). Intravenous and intrarectal administrations of the NANOPEP-6/siRNA complex allowed the delivery of the siRNA in most of the analyzed tissues, excepted brain and ganglions (FIG. 15a). These fluorescence results are directly correlated to a KO of the GAPDH mRNA, demonstrating that NANOPEP-6 delivers an active form of the siRNA in all the tissues and can be efficiently applied by topical administration (FIG. 15b). Intranasal and intratracheal administration allowed the delivery of active siRNA mainly in the lung, liver and kidney and in the brain, with a significant KO of the GAPDH gene in these tissues. In contrast, transdermal administration is limited to the delivery of the siRNA into and through the skin and muscles, but not in the other tissues (FIG. 15c).

Example 6

Optimized Formulations of VEPEP-6/siRNA Complexes

FIG. 16 shows a protocol for obtaining a fresh or a lyophilized formulation of VEPEP-6/siRNA complexes, which show excellent long-term storage stability. The largest batch produced uses 10 mg of siRNA. Before lyophilisation, 5% glucose and/or sucrose have been added to the solution comprising VEPEP-6/siRNA complexes (up to 20% glucose/fructose can be added, wherein the percentage of sugar is calculated as follows: x % of sugar=x g of sugar added in 1 l of solution comprising the complexes or nanoparticles, before lyophilization).

The process illustrated in FIG. 16 does not comprise any purification/separation step, but such a step could possibly be added if needed in a larger production scale.

The stability of the VEPEP-6/siRNA complexes was assessed by HPLC size exclusion chromatography analysis.

VEPEP-6/siRNA samples were incubated at molar ratio 20:1 for 30 min at 25° C., then filtered using a 0.2µ filter and analyzed by size exclusion HPLC chromatography using SEC 3000 after 1, 5, 24 and 96 hrs (FIG. 17, panel A). Lyophilized VEPEP-6/siRNA in 5% glucose, were analyzed after 24 and 96 hr (FIG. 17, panel B). The Percentage of free peptide was estimated. This demonstrated that in the optimized conditions no free peptide is detected after 1 h and only 7% after 24 hr. In any case, no free siRNA has been detected, as measured by quantigen technology (FIG. 17, Panel C) The level of siRNA within the particle was measured after dissociation of the particle with 20% acetonitrile (ACN). Quanti- Gene Assays (Affymetrix) are assays enabling quantitation with single-copy RNA sensitivity at single cell resolution in cells or tissues in singleplex and multiplex assay formats. The results showed that VEPEP-6/siRNA complexes are highly stable in sugar containing buffer.

Further stability experiments showed that the lyophilized VEPEP-6/siRNA complexes are highly stable upon storage at 4° C., since after 5 months, the product retained more than 85% of its original activity (measured as GAPDH silencing in Hela cells).

The same experiments have been performed with VEPEP-6/VEPEP-6/siRNA nanoparticles, and showed the same stability as that observed for the complexes.

Example 7

NANOPEP-6 Promotes Delivery of Multi-siRNA

The therapeutic potential of the NANOPEP-6 technology has been evaluated in vivo with siRNA targeting CDC20 and cyclin B1, a non-redundant mitotic cyclin. Athymic female nude mice (6-8 weeks of age) were subcutaneously inoculated into the flank with $1 \times 10^6$ PAN-1 (pancreas cancer) cells in 100 μl PBS. Five days after tumour implant, animals were treated by intravenous injection, every 4 days, with a solution of 0.1 ml of either phosphate buffer, free Cyc-B1/CDC20 siRNA (50 μg), Cyc-B1 or CDC20 siRNA (2 μg) and both siRNA complexed within NANOPEP-6 particles. The "core" shell of the particles was formed using VEPEP-6 peptide at a molar ratio of 20/1 with a siRNA targeting cycline B1 or CDC20. siRNA stock solutions are in 50 mM Tris, 0.5 mM EDTA buffer or in RNase free water. VEPEP-6 peptides were solubilised in water and stock solution of peptide was sonicated for 10 min in a water bath before complex formation. Then VEPEP-6/siRNA complexes were formed by adding siRNA into the peptide solution and incubating at 37° C. for 20-30 minutes to allow the carrier peptide/siRNA complexes to form. NANOPEP-6 particles contain a VEPEP-6/siRNA "core shell" surrounded by additional VEPEP-6 at a 1/20 molar ratio. Experiments were performed according to national regulations and approved by the local animal experimentation ethical committee. The statistical significance of the results was calculated by Student's t test and p<0.05 considered to be statistically significant. The stock solutions of particles are performed in water and stable for at least three weeks at 4° C. Particles can be lyophilized for long time storage; in that case, 5 to 20% of glucose is added to the particle solution before lyophylization to stabilize the particles during the process. Before administration, the particles are diluted in physiological conditions, in the presence: 0.9% NaCl and 5 to 20% glucose.

The results, illustrated in FIG. 18, show that VEPEP-6 improves siRNA efficacy via systemic IV administration, and that NANOPEP-6 technology allows the delivery of several siRNA mixed together without inducing any toxicity or side effect.

Example 8

NANOPEP-6 Promotes Delivery of miRNA

MicroRNAs (miRNAs) have been implicated in cancer initiation and progression via their ability to affect expression of genes and proteins that regulate cell proliferation and/or cell death. Transcription of the three miRNA miR-34 family members was found to be directly regulated by p53 [1,4]. Restoration of miR-34 may hold significant promise as a novel molecular therapy for several cancers, such as lung cancer, breast cancer, pancreatic cancer, glyoblatome and skin cancer etc. For example, in human pancreatic cancer with loss of p53-miR34, restoration of miR-34 may act via inhibiting pancreatic cancer stem cells [15].

The ability of NANOPEP-6 technology was assessed using the mir-34a microRNA of sequence uggcaguguggguagcugg-uug (SEQ ID No: 26). Dissociation constant of peptide for single stranded miRNA-34 was determined by steady state fluorescence measurement. Fix concentrations of CY5-labelled mi34, was titrated by increasing concentration of peptide and fluorescence changes were monitored at 550 nm upon excitation at 505 nm (FIG. 19, panel A). VEPEP-6 strongly interacts with single stranded miRNA (Kd: 25 nM).

Antiproliferation properties of miR34 have been evaluated onto MCF7 breast cancer cells. Cell lines (from American Type Culture Collection (ATCC)) were cultured in Dulbecco's Modified Eagle's Medium supplemented with 2 mM glutamine, 1% antibiotics (streptomycin 10'000 μg/ml, penicillin, 10,000 IU/ml) and 10% (w/v) foetal calf serum (FCS), at 37° C. in a humidified atmosphere containing 5% $CO_2$. Stock solutions of VEPEP-6a/miRNA34 particles were prepared by complexing 1 μM miRNA34 with VEPEP-6a peptides at a molar ratio of 1/20 for 30 min at 37° C. Lower concentrations of VEPEP-6a-carrier/miRNA (from 500 nM to 1 nM) were obtained by serial dilutions of the stock complexes in PBS, in order to preserve the same VEPEP-6a-carrier/miRNA ratio. 150 000 cells seeded in a 35 mm dish the day prior transfection, were grown to 40% confluence and overlaid with 200 μl of preformed complexes, incubated for 3-5 min, then 1 ml of fresh DMEM containing 16% foetal calf serum (FCS) was added and cells were returned to the incubator for 24 hrs. Cell growth was measured after 4 days. Dose responses of free (grey bars) and VEPEP-6 (white bars) mediated miR-34 have been evaluated. VEPEP-6 strongly improves antiproliferative properties of miR34 with an $IC_{50}$ value of 85 nM (FIG. 19, panel B).

Example 9

Stapled VEPEP-6

Example 9.1

Stapling of VEPEP-6 Carrier Increases Stability of VEPEP-6/Cargoes Complexes 9.1.1. Chemistry In a context completely different from CPPs, hydrocarbon alpha helix stapled peptides have been developed and reported to be more stable and able to enter the cell [16]. The α-helix features 3.6 residues per complete turn, which places the i, i+4, i+7, and i+11 side chains on the same face of the folded structure. The classical strategy to stabilize the α-helical conformation in peptides employs covalent bonds between the i and i+4 or i and i+7 side chain groups (FIG. 20A). VEPEP-6 peptides are stapled in i, i+4 and i, i+7 using hydrocarbon bridged method recently described by Verdine and Hilinski [17] and by Youg-Woo kim et al. [18]. The i, i+4 is the optimal stabilized stapled peptides structure. The stapled are synthetized by solid-phase peptide synthesis (SPPS), using amino acids with acid-labile side chain protecting groups and a base labile fluorenylmetoxycarbonyl protecting group on the backbone amine (FIG. 20B).

Sequences:

```
                                          (SEQ ID No: 27)
ST-VEPEP-6a:
Ac-X₁LFRALWR_SLLRS_SLWRLLWK-cysteamide (SEQ ID No: 28)
ST-VEPEP-6aa:
Ac-X₁LFLARWR_SLLRS_SLWRLLWK-cysteamide (SEQ ID No: 29)
ST-VEPEP-6ab:
Ac-X₁LFRALWS_SLLRS_SLWRLLWK-cysteamide (SEQ ID No: 30)
ST-VEPEP-6ad:
Ac-X₁LFLARWS_SLLRS_SLWRLLWK-cysteamide (SEQ ID No: 31)
ST-VEPEP-6b:
Ac-X₁LFRALWRLLR_SSLWS_SLLWK-cysteamide (SEQ ID No: 32)
ST-VEPEP-6ba:
Ac-X₁LFLARWRLLR_SSLWS_SLLWK-cysteamide (SEQ ID No: 33)
ST-VEPEP-6bb:
Ac-X₁LFRALWRLLS_SSLWS_SLLWK-cysteamide (SEQ ID No: 34)
ST-VEPEP-6bd:
Ac-X₁LFLARWRLLS_SSLWS_SLLWK-cysteamide (SEQ ID No: 35)
ST-VEPEP-6c:
Ac-X₁LFAR_SLWRLLRS_SLWRLLWK-cysteamide
```

9.1.2. Stapling Increases the Interaction with Cargoes

The impact of the stabilization of the helical structure of the VEPEP-6 peptides on their ability to interact with nucleic acid cargoes was evaluated. Since the binding of cargoes to cell-penetrating peptides implies a certain flexibility of the CPP, the increased rigidity of the stapled CPP could lead to a decrease affinity for the cargo.

Binding of nucleic acid to ST-VEPEP-6aa was monitored by fluorescence spectroscopy using both TRP-intrinsic and fluorescently labelled nucleic acids. Dissociation constants were calculated from data fitting. Nucleic acids used were double stranded siRNA (19/19 or 25/25) and single stranded DNA (36 mer).

FIG. 21 shows that ST-VEPEP-6aa strongly interacts with single and double stranded nucleic acids with dissociation constant of 4 and 7 nM, 2-fold lower than that obtained for the non modified peptide. The same efficacy was observed with the other ST-VEPEP sequences.

The dissociation of preformed siRNA/ST-VEPEP-6 complexes was then analysed in the presence of heparan sulphate. Heparan sulphate constitutes one of major components of the proteoglycan. Kinetic of complexes dissociation is reported in FIG. 22, using FITC-labelled siRNA associated to ST-VEPEP-6 or VEPEP-6. Dissociation was triggered by adding increasing Heparan sulphate concentrations. Data demonstrated that ST-VEPEP-/siRNA and VEPEP-6/siRNA are dissociated with a concentration of 560 µM and 120 µM respectively, suggesting that complexes formed with stapled peptide are 5 fold more stable

Example 9.2

Stapling Increased the Potentiality in Cellulo and in Vivo with Cargoes

9.2.1. ST-VEPEP-6-Mediated Delivery of siRNA in Different Cell Lines

ST-VEPEP-6 peptides have been used for the delivery of siRNA into three different cell lines, including adherent (Hela, HEK), suspension and challenging cell lines such as primary (Jurkat) and stem cell lines (mES). Stock solutions of ST-VEPEP-6/siRNA particles were prepared by complexing 100 nM siRNA with ST-VEPEP-6 peptides at a molar ratio of 1/20 for 30 min at 37° C. Lower concentrations of ST-VEPEP-6-carrier/siRNA (from 20 nM to 0.125 nM) were obtained by serial dilutions of the stock complexes in PBS, in order to preserve the same ST-VEPEP-6-carrier/siRNA ratio. Dose-response experiments performed on different cultured cells revealed that ST-VEPEP-6-mediated delivery of siRNA (GAPDH) induced a robust downregulation (EC50) of GAPDH mRNA level measured by quantigen technology (Table 7). ST-VEPEP-6 are between 2 to 6 fold more efficient than unmodified peptides and exhibit a 2-fold lower toxicity (EC50) as measured by MTT assays.

TABLE 7

| Cell Lines | IC50 GAPDH KD VEPEP-6 | EC50 GAPDH VEPEP-6 | IC50 GAPDH KD VEPEP-6 | EC50 GAPDH VEPEP-6 |
|---|---|---|---|---|
| Hela | 1.2 nM | 200 µM | 0.8 nM | >500 µM |
| Jurkat | 5.6 nM | 200 µM | 1.4 nM | >500 µM |
| mES | 7.5 nM | 200 µM | 1.7 nM | >500 µM |
| HEK | 4.2 nM | 200 µM | 0.9 nM | >500 µM |

9.2.2. ST-VEPEP-6 Mediated Delivery of siRNA In Vivo

ST-VEPEP-6 Cyclin B1/siRNA delivery was assessed upon systemic injection. Athymic female nude mice were subcutaneously inoculated into the flank with $1 \times 10^6$ HT-29 (lung-tumor). 20 days after tumour implant, when tumour size reached about 100 mm³, animals were treated by intravenous injections, every 4 days, with either saline buffer solution (PBS), free siRNA, Cyc-B1 siRNA at 3 µg and 5 µg complexed with ST-VEPEP-6 or VEPEP-6 at a 1/20 molar ratio (FIG. 23). Curves show the mean value of tumor size in a cohort of three animals and neither animal death nor any sign of toxicity were observed. Data demonstrated that stapling of the peptide improves in vivo response by a factor of 2 and allows the use of lower concentrations of siRNA.

REFERENCES

[1] D J. Glover, H J. Lipps, D A. Jans, Towards safe, non-viral therapeutic gene expression in humans. Nat. Rev. Genet. 6 (2005) 299-310

[2] K A. Whitehead, R. Langer, D G. Anderson, Knocking down barriers: advances in siRNA delivery. Nat Rev Drug Discov. 8 (2009) 129-138.

[3] Ü Langel, Handbook of Cell-Penetrating Peptides: (Eds.: U. Langel) CRC Taylor & Francis, Boca Raton (2007).

[4] F. Heitz, M C. Morris, G. Divita, Twenty years of cell-penetrating peptides: from molecular mechanisms to therapeutics; British Journal of Pharmacology 157 (2009) 195-206.

[5] S. Deshayes, M C Morris, F. Heitz, G. Divita. Delivery of proteins and nucleic acids using a non-covalent peptide-based strategy. Adv Drug Deliv Rev. 60 (2008) 537-547.
[6] S. Deshayes, M C. Morris, G. Divita, F. Heitz Cell-penetrating peptides: tools for intracellular delivery of therapeutics, Cell Mol Life Sci. 62 (2005) 1839-1849.
[7] M C. Morris, P. Vidal, L. Chaloin, F. Heitz, G Divita A new peptide vector for efficient delivery of oligonucleotides into mammalian cells, Nucleic Acids Res. (1997) 2730-2736.
[8] M C. Morris, J. Depollier, J. Mery, F. Heitz, G. Divita A peptide carrier for the delivery of biologically active proteins into mammalian cells, Nat. Biotechnol. 19 (2001) 1173-1176.
[9] Thomas, A., Deshayes, S., Decaffineyer, M., Van Eyck, M. H., Charloteaux, B. & Brasseur, R. Prediction of peptide structure: how far are we? *Proteins* 65, 889-897 (2006).
[10] Mery J, Brugidou J, Derancourt J. Disulfide bond as peptide-resin linkage in Boc-Bzl SPPS, for potential biochemical applications, Pept Res. 1992 July-August; 5(4): 233-40.
[11] L. Crombez, M. C. Morris, S. Dufort, G. Aldrian-Herrada, Q. Nguyen, G. Mc Master, J. L. Coll, F. Heitz, G. Divita, Targeting cyclin B1 through peptide-based delivery of siRNA prevents tumour growth, Nucleic Acids Res. 37 (2009) 4559-4569.
[12] L. Crombez, G. Aldrian-Herrada, K. Konate, Q. N. Nguyen, G. K. McMaster, R. Brasseur, F. Heitz, G. Divita, A new potent secondary amphipathic cell-penetrating peptide for siRNA delivery into mammalian cells, Mol. Ther. 17 (2009) 95-103.
[13] Gondeau, C., Chaloin-Gerbal, S., Bello, P., Aldrian-Herrada, G., Morris M. C. & Divita G. (2005) Design of a novel class of peptide inhibitors of cyclin-dependent kinase/cyclin activation. J. Biol. Chem., 280 (14): 13793-13800.
[14] He L, He X, Lim L P, de Stanchina E, Xuan Z, Liang Y, Xue W, Zender L, Magnus J, Ridzon D, Jackson A L, Linsley P S, Chen C, Lowe S W, Cleary M A, Hannon G J. (2007) A microRNA component of the p53 tumour suppressor network. Nature.; 447(7148): 1130-4.
[15] Ji Q, Hao X, Zhang M, Tang W, Yang M, Li L, Xiang D, Desano J T, Bommer G T, Fan D, Fearon E R, Lawrence T S, Xu L. (2009) MicroRNA miR-34 inhibits human pancreatic cancer tumor-initiating cells. PLoS One. 4(8): e6816.
[16] Zhang H, Curreli F, Zhang X, Bhattacharya S, Waheed A A, Cooper A, Cowburn D, Freed E O, Debnath A K. (2011) Antiviral activity of α-helical stapled peptides designed from the HIV-1 capsid dimerization domain. Retrovirology. 2011 May 3; 8:28.
[17] Verdine, G. L. and Hilinski, G. J. (2012), Stapled peptides for intracellular drug targets. Methods in Enzymology, vol 503, p 3-33.
[18] Young-Woo Kim, Grossmann, T. N., and Verdine, G. L. (2011), Synthesis of all-hydrocarbon stapled α-helical peptides by ring-closing olefin methathesis. Nature protocols, vol. 6, No. 6, p. 761-771.

The invention claimed is:

1. A cell-penetrating peptide comprising an amino acid sequence selected from the group consisting of $X_1LX_2RALWX_9LX_3X_9X_4LWX_9LX_5X_6X_7X_8$ (SEQ ID NO: 36), $X_1LX_2LARWX_9LX_3X_9X_4LWX_9LX_5X_6X_7X_8$ (SEQ ID NO: 37) and $X_1LX_2ARLWX_9LX_3X_9X_4LWX_9LX_5X_6X_7X_8$ (SEQ ID NO: 38), wherein $X_1$ is beta-A or S, $X_2$ is F or W, $X_3$ is L, W, C or I, $X_4$ is S, A, N or T, $X_5$ is L or W, $X_6$ is W or R, $X_7$ is K or R, $X_8$ is A or none, and $X_9$ is R or S.

2. The cell-penetrating peptide of claim 1, comprising an amino acid sequence $X_1LX_2RALWRLX_3RX_4LWRLX_5X_6X_7X_8$ (SEQ ID NO: 13), wherein X1 is beta-A or S, $X_2$ is F or W, $X_3$ is L, W, C or I, $X_4$ is S, A, N or T, $X_5$ is L or W, $X_6$ is W or R, $X_7$ is K or R, and $X_8$ is A or none.

3. The cell-penetrating peptide of claim 1 comprising an amino acid sequence of $X_1LX_2RALWRLX_3RX_4LWRLX_5X_6KX_7$ (SEQ ID NO: 14), wherein $X_1$ is beta-A or S, $X_2$ is F or W, $X_3$ is L or W, $X_4$ is S, A or N, $X_5$ is L or W, $X_6$ is W or R, $X_7$ is A or none.

4. The cell-penetrating peptide of claim 2, wherein the amino acid sequence is selected from the group consisting of

```
                                         (SEQ ID No: 7)
X1LFRALWRLLRX2LWRLLWX3, (SEQ ID No: 8)
X1LWRALWRLWRX2LWRLLWX3A, (SEQ ID No: 9)
X1LWRALWRLX4RX2LWRLWRX3A, (SEQ ID No: 10)
X1LWRALWRLWRX2LWRLWRX3A, (SEQ ID No: 11)
X1LWRALWRLX5RALWRLLWX3A,
and (SEQ ID No: 12)
X1LWRALWRLX4RNLWRLLWX3A,
``` wherein $X_1$ is beta-A or S, $X_2$ is S or T, $X_3$ is K or R, $X_4$ is L, C or I and $X_5$ is L or I.

5. The cell-penetrating peptide of claim 1, further comprising, covalently linked to the N-terminal end of the amino acid sequence, one or more chemical entities selected from the group consisting of an acetyl, a fatty acid, a cholesterol, a poly-ethylene glycol, a nuclear localization signal, nuclear export signal, an antibody, a polysaccharide and a targeting molecule.

6. The cell-penetrating peptide of claim 1, further comprising, covalently linked to the C-terminal end of said amino acid sequence, one or more groups selected from the group consisting of a cysteamide, a cysteine, a thiol, an amide, a nitrilotriacetic acid optionally substituted, a carboxyl, a linear or ramified $C_1$-$C_6$ alkyl optionally substituted, a primary or secondary amine, an osidic derivative, a lipid, a phospholipid, a fatty acid, a cholesterol, a poly-ethylene glycol, a nuclear localization signal, a nuclear export signal, an antibody, a polysaccharide and a targeting molecule.

7. The cell-penetrating peptide of claim 1, which is selected from the group consisting of:

```
                                         (SEQ ID No: 1)
VEPEP-6a:
Ac-X1LFRALWRLLRSLWRLLWK-cysteamide, (SEQ ID No: 2)
VEPEP-6b:
Ac-X1LWRALWRLWRSLWRLLWKA-cysteamide, (SEQ ID No: 3)
VEPEP-6c:
Ac-X1LWRALWRLLRSLWRLWRKA-cysteamide, (SEQ ID No: 4)
VEPEP-6d:
Ac-X1LWRALWRLWRSLWRLWRKA-cysteamide, (SEQ ID No: 5)
VEPEP-6e:
Ac-X1LWRALWRLLRALWRLLWKA-cysteamide,
and (SEQ ID No: 6)
VEPEP-6f:
Ac-X1LWRALWRLLRNLWRLLWKA-cysteamide,
``` wherein $X_1$ is beta-A or S.

8. The cell-penetrating peptide of claim 1, further comprising a hydrocarbon linkage between two residues at positions 8 and 12.

9. The cell-penetrating peptide of claim 1, which is selected from the group consisting of:

```
                                         (SEQ ID No: 27)
ST-VEPEP-6a:
Ac-X1LFRALWRSLLRSSLWRLLWK-cysteamide, (SEQ ID No: 28)
ST-VEPEP-6aa:
Ac-X1LFLARWRSLLRSSLWRLLWK-cysteamide, (SEQ ID No: 29)
ST-VEPEP-6ab:
Ac-X1LFRALWSSLLRSSLWRLLWK-cysteamide, (SEQ ID No: 30)
ST-VEPEP-6ad:
Ac-X1LFLARWSSLLRSSLWRLLWK-cysteamide, (SEQ ID No: 31)
ST-VEPEP-6b:
Ac-X1LFRALWRLLRSSLWSSLLWK-cysteamide, (SEQ ID No: 32)
ST-VEPEP-6ba:
Ac-X1LFLARWRLLRSSLWSSLLWK-cysteamide, (SEQ ID No: 33)
ST-VEPEP-6bb:
Ac-X1LFRALWRLLSSSLWSSLLWK-cysteamide, (SEQ ID No: 34)
ST-VEPEP-6bd:
Ac-X1LFLARWRLLSSSLWSSLLWK-cysteamide,
and (SEQ ID No: 35)
ST-VEPEP-6c:
Ac-X1LFARSLWRLLRSSLWRLLWK-cysteamide,
``` wherein $X_1$ is beta-A or S and wherein the residues followed by an inferior "S" are linked by a hydrocarbon linkage.

10. A complex comprising a cell-penetrating peptide according to claim 1 and a cargo selected from the group consisting of a nucleic acid and a hydrophobic molecule.

11. The complex of claim 10, wherein said cargo is a siRNA or a mix of siRNAs selected to silence a target mRNA.

12. The complex of claim 10, wherein said cargo is a miRNA or a mix of miRNAs.

13. The complex of claim 10, wherein the size of the complex is between 50 and 300 nm.

14. A nanoparticle comprising a complex according to claim 10, coated by a layer of peripheral cell-penetrating peptides, wherein said peripheral cell-penetrating peptides have a peptide sequence different from SEQ ID NO: 13.

15. A nanoparticle comprising a core which comprises a cargo complexed to a first entity selected from the group consisting of cell-penetrating peptides, liposomes, polycationic structures and carbon nanoparticles, wherein said core is coated by a cell-penetrating peptide according to claim 1.

16. The nanoparticle of claim 15, wherein said first entity is a cell-penetrating peptide selected from the group consisting of CADY, MPG, PEP-1, PPTG1, and poly Arginine motif.

17. The nanoparticle of claim 14 or 15, wherein the size of the nanoparticle is between 80 and 400 nm.

18. The complex of claim 10, wherein the cell-penetrating peptide comprises an acetyl group covalently linked to its N-terminus, and/or a cysteamide group covalently linked to its C-terminus.

19. The complex of claim 10, wherein the cell-penetrating peptide is bound to a targeting molecule.

20. The complex or nanoparticle of any one of claims 10, 14 and 15, which has been lyophilized in the presence of a sugar.

21. The complex or nanoparticle according to claim 20, wherein said sugar is sucrose or glucose or a mix thereof, present in a concentration ranging from 5% to 20% before lyophilization.

22. A therapeutic or diagnostic composition comprising a complex or a nanoparticle according to any one of claims 10, 14 and 15.

23. The composition of claim 22, which is formulated for intravenous, subcutaneous, intratumoral, topical, intrarectal, intranasal, or intradermal administration, or for administration via a mouth spray.

24. A method for delivering a molecule into a cell in vitro, comprising a step of putting said cell into contact with a complex comprising said molecule and cell-penetrating peptides according to claim 1.

25. The cell-penetrating peptide of claim 5, wherein the one or more chemical entities is a cholesterol.

26. The cell-penetrating peptide of claim 5, wherein the one or more chemical entities is a fatty acid.

27. The cell-penetrating peptide of claim 5, wherein the one or more chemical entities is a targeting molecule.

28. The cell-penetrating peptide of claim 6, wherein the one or more groups is a fatty acid.

29. The cell-penetrating peptide of claim 6, wherein the one or more groups is a targeting molecule.

30. The cell-penetrating peptide of claim 7, which is
VEPEP-6a: Ac-$X_1$LFRALWRLLRSLWRLLWK-cysteamide (SEQ ID NO: 1),
wherein $X_1$ is beta-A or S.

31. The cell-penetrating peptide of claim 7, which is
VEPEP-6b: Ac-$X_1$ LWRALWRLWRSLWRLLWKA-cysteamide (SEQ ID NO: 2),
wherein $X_1$ is beta-A or S.

32. A nanoparticle comprising a complex according to claim 18, coated by a layer of peripheral cell-penetrating peptides, wherein said peripheral cell-penetrating peptides have a peptide sequence different from SEQ ID NO: 13.

33. The nanoparticle of claim 14, wherein at least part of the peripheral cell-penetrating peptides are bound to a targeting molecule.

34. The nanoparticle of claim 15, wherein at least part of the cell-penetrating peptides coating the core are bound to a targeting molecule.

* * * * *